US007373199B2

(12) United States Patent
Sackellares et al.

(10) Patent No.: US 7,373,199 B2
(45) Date of Patent: May 13, 2008

(54) OPTIMIZATION OF MULTI-DIMENSIONAL TIME SERIES PROCESSING FOR SEIZURE WARNING AND PREDICTION

(75) Inventors: James Chris Sackellares, Gainesville, FL (US); Leonidas D. Iasemidis, Scottsdale, AZ (US); Deng-Shan Shiau, Gainesville, FL (US); Linda Dance, Gainesville, FL (US)

(73) Assignees: University of Florida Research Foundation, Inc., Gainesville, FL (US); Arizona Board of Regents, Tempe, AR (US)

( * ) Notice: Subject to any disclaimer, the term of this patent is extended or adjusted under 35 U.S.C. 154(b) by 545 days.

(21) Appl. No.: 10/648,354

(22) Filed: Aug. 27, 2003

(65) Prior Publication Data

US 2004/0122335 A1 Jun. 24, 2004

Related U.S. Application Data

(60) Provisional application No. 60/414,364, filed on Sep. 30, 2002, provisional application No. 60/406,063, filed on Aug. 27, 2002.

(51) Int. Cl.
    *A61B 5/04* (2006.01)
(52) U.S. Cl. ..................................... 600/544
(58) Field of Classification Search ............... 600/544, 600/545, 300, 301
    See application file for complete search history.

(56) References Cited

U.S. PATENT DOCUMENTS 5,365,939 A * 11/1994 Ochs .................... 600/545

| | | |
|---|---|---|
| 5,857,978 A | 1/1999 | Hively et al. |
| 5,995,868 A | 11/1999 | Dorfmeister et al. |
| 6,061,593 A | 5/2000 | Fischell et al. |
| 6,304,775 B1 | 10/2001 | Iasemidis et al. |
| 6,507,754 B2 | 1/2003 | Le Van Quyen et al. |

FOREIGN PATENT DOCUMENTS

WO    WO 01/21067    *    3/2001

OTHER PUBLICATIONS

Iasemidis et al., "Phase Space Topography of the Electrocorticogram and the Lyapunov Exponent in Partial Seizures," Brain Topography, vol. 2, No. 3, pp. 187-201 (1990).

(Continued)

*Primary Examiner*—Robert L Nasser
(74) *Attorney, Agent, or Firm*—Alston & Bird LLP

(57) ABSTRACT

Characterizing the behavior of a chaotic, multi-dimensional system is achieved by measuring each of a number of signals associated with the system, and generating therefrom, a spatio-temporal response based on each signal. Chaoticity profiles are then generated for each spatio-temporal response. Over a period of time, a determination is made as to whether a certain level of dynamic entrainment and/or disentrainment exists between the chaoticity profiles associated with one or more critical channel groups of a selected predictor, where a predictor represents a given number of critical channel groups "x", a given number of channels per group "y", and a total number of channels N. Characterizing the behavior of the system is based on this determination.

41 Claims, 15 Drawing Sheets

OTHER PUBLICATIONS

Pincus, "Approximate Entropy as a Measure of System Complexity," Proceedings of the National Academy of Science of the United States of America, vol. 88, pp. 2297-2301 (1991).

J.C. Sackellares et al., "Epileptic Seizures as Neural Resetting Mechanisms," Epilepsia, vol. 38, Suppl. 3, p. 189, (1997).

L. D. Iasemidis et al., "Dynamical Resetting of Human Brain at Epileptic Seizures: Application of Nonlinear Dynamics and Global Optimization Techniques," IEEE Transactions on Biomedical Engineering, vol. 51, No. 3, pp. 493-506, (2004).

Wolf et al., "Determining Lyapunov Exponents from a Time Series," Physica D., vol. 16D, pp. 285-317 (1985).

Eckmann et al. "Lyapunov Exponents from Time Series," Physical Review A, vol. 34, No. 6, pp. 4971-4972 (1986).

Iasemidis et al., "Adaptive Epileptic Seizure Prediction System," IEEE Transactions in Biomedical Engineering, vol. 50, No. 5, pp. 616-627, (2003).

Iasemidis et al., "Prediction of Human Epileptic Seizures Based on Optimization and Phase Changes of Brain Electrical Activity," Optimization Methods and Software, vol. 18, No. 1, pp. 81-104, (2003).

Iasemidis et al., "Seizure Warning Algorithm Based on Spatiotemporal Dynamics of Intracranial EEG," Mathematical Programming, vol. 101, No. 2, pp. 365-385, (2004).

\* cited by examiner

OPTIMIZATION OF MULTI-DIMENSIONAL TIME SERIES PROCESSING FOR SEIZURE WARNING AND PREDICTION

RELATED PATENTS

This patent application relates to commonly assigned U.S. Pat. No. 6,304,775, which issued on Oct. 16, 2001. It is incorporated herein by reference in its entirety. This application also claims priority from: U.S. Provisional Application No. 60/414,364 filed in the U.S. Patent and Trademark Office on 30 Sep. 2002; and U.S. Provisional Application No. 60/406,063 filed in the U.S. Patent and Trademark Office on 27 Aug. 2002.

STATEMENT REGARDING FEDERALLY SPONSORED RESEARCH AND DEVELOPMENT

The research and development effort associated with the subject matter of this patent application was supported by the Department of Veterans Affairs and by the National Institute of Biomedical Imaging and Bioengineering of the National Institutes of Health (NIBIB/NIH) under grant no. 8R01EB002089-03.

FIELD OF INVENTION

The present invention involves the field of signal processing. More particularly, the present invention involves the processing of time series signals associated with multi-dimensional systems, such as the electrical and/or electromagnetic signals generated by the brain.

BACKGROUND

A multidimensional system is a system that exhibits behavior autonomously or as a function of multiple variables in response to a system input. A chaotic system is one that exhibits chaotic behavior (i.e., behavior characterized by random responses) during normal operation. The brain is an example of a multidimensional system that also exhibits chaotic behavior during normal operation. In a relatively significant percentage of the human population, the brain experiences periodic, abnormal episodes characterized by non-chaotic behavior. This abnormal behavior may be caused by a wide variety of conditions. Epilepsy is one of these conditions.

Epilepsy is a chronic disorder characterized by recurrent brain dysfunction caused by paroxysmal electrical discharges in the cerebral cortex. At any given time, Epilepsy affects approximately 50 million people worldwide. If untreated, an individual afflicted with epilepsy is likely to experience repeated seizures, which typically involve some level of impaired consciousness. Some forms of epilepsy can be successfully treated through medical therapy. However, medical therapy is less effective with other forms of epilepsy, including Temporal Lobe Epilepsy (TLE) and Frontal Lobe Epilepsy (FLE). With TLE and FLE, removing the portion of the hippocampus and/or cerebral cortex responsible for initiating the paroxysmal electrical discharges, known as the epileptogenic focus, is sometimes performed in an effort to control the seizures.

For quite some time, the medical community has attempted to develop techniques that provide seizure prediction and/or seizure warning, where seizure prediction will be understood to involve a long-range forecast of seizure-onset time, and seizure warning will be understood to involve a long-range indication of conditions conducive to an impending seizure. Any such technique would certainly have numerous clinical and non-clinical application. For example, in order to more effectively treat certain Epilepsy patients, such a technique might be used in conjunction with a device, perhaps an implanted device, designed to deliver a dosage of anti-seizure medication into the patient's bloodstream for the purpose of averting an impending seizure.

In another example, such a technique could be used during pre-surgical evaluations to assist in pinpointing the epileptogenic focus, which is to be removed during surgery. It is understood that during a seizure, blood flow to the epileptogenic focus significantly increases. If certain radio-labeled ligands are injected into the patient's bloodstream in a timely manner, it is possible to monitor that increased blood flow using radiography, thereby allowing a physician to accurately pinpoint the boundaries of the epileptogenic focus. A true seizure prediction and/or warning technique would provide an indication of an impending seizure well in advance and provide sufficient time to prepare for and administer, for example, the aforementioned radiography ligand.

One of the most important tools for evaluating the physiological state of the brain is the electroencephalogram (EEG). The standard for analyzing and interpreting an EEG is visual inspection of the graphic tracing of the EEG by a trained clinical electroencephalographer. However, there is no established method for predicting seizure onset or for providing a seizure warning well before seizure onset by visually analyzing an EEG. Moreover, the use of traditional signal processing techniques on EEG signals has likewise yielded little practical information. These traditional techniques are limited in their effectiveness because the brain is a multidimensional system that produces nonlinear signals with spatial as well as temporal properties. Thus, traditional signal processing techniques employing standard, linear, time series analysis methods cannot detect the spatio-temporal properties that are critical in providing effective seizure warning and prediction.

Commonly assigned U.S. Pat. No. 6,304,775, however, describes systems and methods capable of effectively generating true seizure warnings and predictions well in advance of impending seizures. The systems and methods described in this patent take advantage of the spatio-temporal characteristics exhibited by certain sites within the brain, when compared with the spatio-temporal characteristics exhibited by other sites within the brain, as these characteristics are noticeably different prior to an impending seizure as compared to the spatio-temporal characteristics exhibited by these same sites during seizure free intervals. In fact, these spatio-temporal characteristics may be noticeable hours, and in some cases, days before the occurrence of a seizure. As such, the systems and methods described in U.S. Pat. No. 6,304,775 use these differences as a seizure transition indicator.

U.S. Pat. No. 6,304,775 specifically describes, among other things, a technique that provides timely impending seizure warning (ISW), seizure susceptibility period detection (SSPD) and time to impending seizure prediction (TISP). The technique involves acquiring electrical or electromagnetic signals generated by the brain, where each signal corresponds to a single EEG electrode or channel. Each signal is pre-processed (e.g., amplified, filtered, digitized) and sampled. This results in a sequence of digital samples for each signal over a period of time, referred therein as an epoch. The samples are then used to generate a phase space portrait for each signal epoch.

For each phase space portrait, a parameter reflecting rate of divergence is computed based on adjacent trajectories in the phase space, where rate of divergence, in turn, reflects the chaoticity level of the corresponding signal. In U.S. Pat. No. 6,304,775, the parameter that is used for this purpose is the short-term, largest Lyapunov exponent ($STL_{MAX}$).

In general, the $STL_{MAX}$ values associated with each EEG signal (i.e., each EEG channel) are compared to the $STL_{MAX}$ values associated with each of the other channels. In U.S. Pat. No. 6,304,775, the comparisons are preferably achieved by applying a T-statistic, which results in a sequence of statistical values, or T-index values, for each channel pair, where a sequence of T-index values represents a level of correlation or entrainment between the spatio-temporal response associated with the two channels that make up each channel pair.

The technique, when first employed, goes through an initialization period. During this initialization period, a number of "critical" channel pairs is identified, where a critical channel pair is defined in U.S. Pat. No. 6,304,775 as a pair of channels that exhibits a relatively high level of entrainment (i.e., relatively low T-index values for a predefined period of time) prior to seizure onset.

During the initialization period, a patient may experience one or more seizures. After each, the list of critical channel pairs is updated. Eventually, the list of critical channel pairs is considered sufficiently refined, and the initialization period is terminated. Thereafter, the ISW, SSPD and TISP functions may be activated and the T-index values associated with the critical channel pairs are monitored and employed in generating timely ISWs, SSPDs and/or TISPs.

Even after the initialization period is over, the list of critical channel pairs is updated following each seizure. Updating the list is important because the brain does not necessarily reset itself completely after each seizure and because the physiological state of the patient may change over time. As a result, the spatio-temporal characteristics associated with any given channel may change over time. Thus, a channel pair previously identified as a critical channel pair may need to be removed from the list of critical channel pairs, while a channel pair that was not previously identified as a critical channel pair may need to be added to the list and subsequently used in generating a next ISW, SSPD or TISP.

SUMMARY OF THE INVENTION

The present invention builds upon U.S. Pat. No. 6,304,775. It does so by optimizing the selection/reselection of critical channels, the spatio-temporal responses of which are ultimately used as a basis for generating ISWs, SSPDs and TISPs. The present invention achieves this optimization in several ways.

Since the issuance of U.S. Pat. No. 6,304,775, it has been determined that disentrainment of the spatio-temporal responses associated with two or more channels is an important factor to consider when selecting critical channels. In U.S. Pat. No. 6,304,775, only entrainment was taken into consideration. Thus, the present invention provides for a more effective selection of critical channels by taking into consideration both entrainment and disentrainment data and, therefore, a more effective generation of ISWs, SSPDs and TISPs.

It has also been determined that two or more channels may exhibit a significant level of entrainment. Regardless, no seizure follows. In fact, the conditions precedent to issuing an ISW may exist, though no seizure follows. These events where the conditions are the same as the preictal conditions of a true seizure, but no seizure actually develops, are referred to herein as "near seizures." Despite the absence of a seizure, the T-index values preceding these "near-seizure" events are valuable. Accordingly, the present invention provides a more efficient and effective critical channel selection process by taking into consideration entrainment data associated with all seizure-related events, including seizures and "near-seizure" events.

The present invention further optimizes the critical channel selection process by limiting the amount of data that is processed. After detecting a seizure-related event (i.e., a seizure or near-seizure event), the present invention processes a limited amount of statistical data (e.g., T-index values) occurring within a predefined time window preceding and, in the case of a seizure, following the seizure-related event. As such, the processing of this data and the subsequent selection of critical channels is accomplished more quickly and efficiently.

Accordingly, it is an objective of the present invention to provide ISWs, SSPDs and TISPs well in advance of seizure onset, based on an efficient and effective selection of critical channels.

It is another objective of the present invention to utilize the ISW, SSPD and TISP features of the present invention in conjunction with seizure intervention techniques, such as anti-seizure drug medication intervention therapy and neuro-stimulation therapy.

It is still another objective of the present invention to utilize the ISW, SSPD and TISP features of the present invention in conjunction with various in-patient applications, including pre-surgical evaluation and diagnosis procedures.

In accordance with a first aspect of the present invention, the above-identified and other objects are achieved through a method of analyzing a multidimensional system. The method involves acquiring a plurality of signals, each representing a corresponding channel associated with a different spatial location of the multidimensional system. A phase space representation is generated for each channel, as a function of the corresponding one of the plurality of signals, and thereafter, a signal profile is generated for each phase space representation, each signal profile reflecting a rate of divergence of the corresponding phase space representation. For a selected predictor, chosen from amongst a number of possible predictors, a signal profile is derived for one or more critical channel groups, each signal profile reflecting a level of correlation between the channels of each critical channel group. Ultimately, the state dynamics of the multidimensional system are characterized as a function of the signal profile associated with at least one critical channel group.

In accordance with a another aspect of the present invention, the above-identified and other objects are achieved through a method of providing seizure warnings. This aspect of the present invention involves, more specifically, acquiring a plurality of time-series signals, each associated with a different location of the brain, and where each signal and its corresponding location constitute a corresponding channel. A spatio-temporal response is generated for each channel as a function of a corresponding one of the time-series signals. Then, a signal profile is generated for each spatio-temporal response, each signal profile comprising a sequence of chaoticity values reflecting a rate of divergence of the corresponding spatio-temporal response. One or more seizure-related events are then detected and, after each, a level of entrainment associated with each channel group for each of a plurality of predictors is determined. Based on the level of entrainment associated with each channel group, a number of critical channel groups for each predictor is determined. A selected predictor is ultimately chosen from amongst the plurality of predictors based on the level of entrainment of the critical channel groups associated with each predictor. Thereafter, the method involves determining when the level of entrainment associated with one or more of the critical channel groups of the selected predictor is statistically significant, and if it is so determined, generating a seizure warning.

In accordance with a yet another aspect of the present invention, the above-identified and other objects are achieved through a method of providing seizure warnings. This aspect of the present invention specifically involves choosing a selected predictor from amongst a plurality of predictors and acquiring a plurality of time-series signals, each signal associated with a different location of the brain, where each signal and its corresponding location constitute a corresponding channel. A spatio-temporal response is then generated for each channel as a function of a corresponding one of the time-series signals. Thereafter, a signal profile is generated for each spatio-temporal response, each signal profile comprising a sequence of chaoticity values reflecting a rate of divergence of the corresponding spatio-temporal response. A determination is then made as to whether the level of entrainment associated with one or more critical channel groups of the selected predictor is statistically significant, and if it is so determined, a seizure warning is generated.

In accordance with still another aspect of the present invention, the above-identified and other objects are achieved through an apparatus that provides seizure interdiction. The apparatus includes a plurality of sensors, each configured for acquiring a time-series signal associated with a corresponding location of a patient's brain, and processing means for generating a seizure warning based on the time-series signals. The processing means includes means for receiving the time-series signals, where each time-series signal along with the corresponding location of the patient's brain constitutes a separate channel. The processing means also includes means for generating a phase space representation for each channel as a function of the corresponding one of the plurality of signals; means for generating a signal profile for each phase space representation, each signal profile reflecting a rate of divergence of the corresponding phase space representation; and means for deriving a signal profile for each of a number of critical channel groups associated with a selected predictor, chosen from amongst a number of predictors, where each signal profile reflects a level of entrainment among the channels of each critical channel group. The processing means further includes means for determining whether a level of entrainment associated with one or more critical channel groups of the selected predictor is statistically significant and means for generating a seizure warning if it is determined that the level of entrainment associated with one or more critical channel groups of the selected predictor is statistically significant. A seizure interdiction device is coupled to the processing means, where the seizure interdiction device includes means for delivering antiseizure treatment to the patient if a seizure warning signal is generated.

BRIEF DESCRIPTION OF THE FIGURES

The objects and advantages of the present invention will be understood by reading the following detailed description in conjunction with the drawings in which.

DETAILED DESCRIPTION OF THE INVENTION

Figure 1:
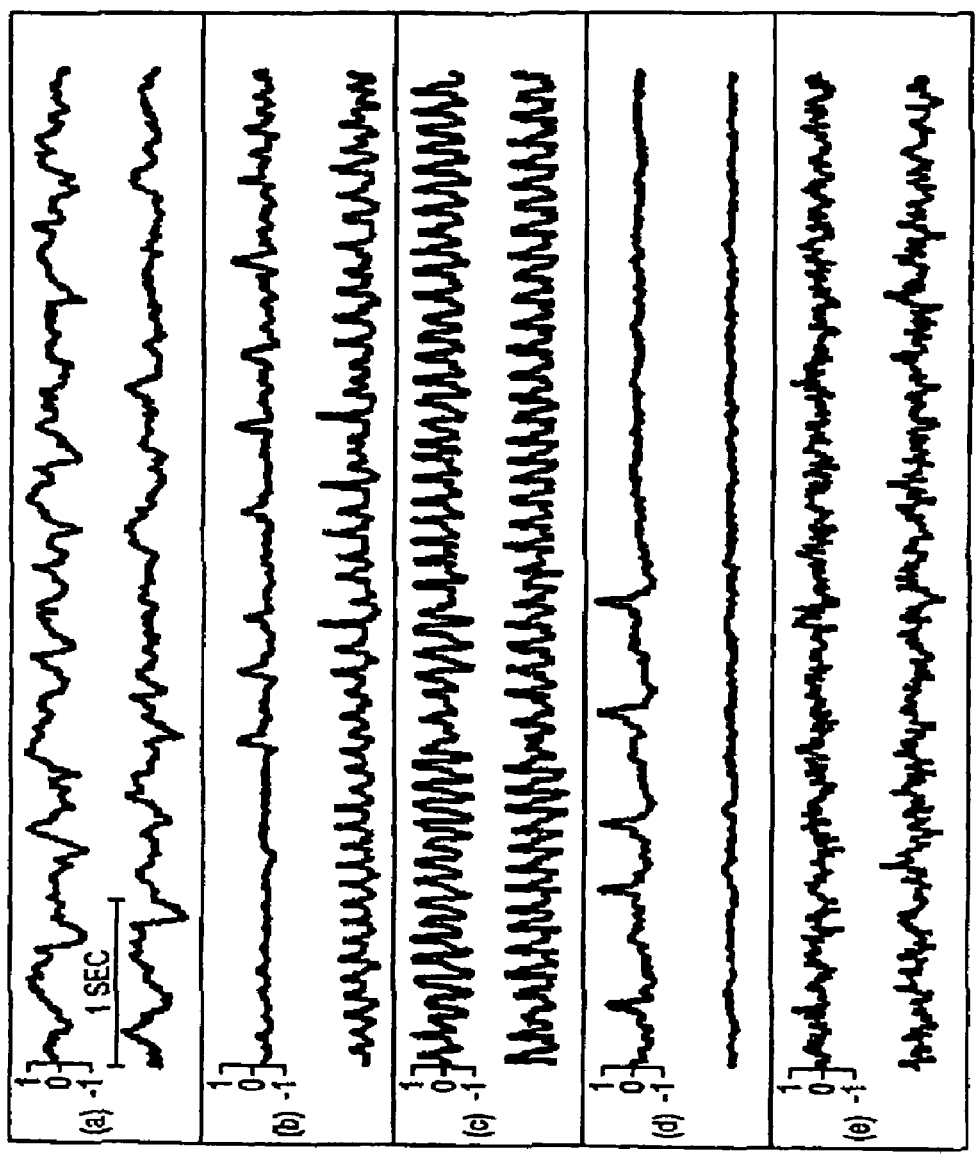
FIGS. 1(a)-(e) illustrates an exemplary, single channel EEG signal as a patient transitions through the various stages of an epileptic seizure.

Seizures, including epileptic seizures, are multiple stage events. The various stages include a preictal stage, an ictal stage, a postictal stage and an interictal stage. FIGS. 1(a-e) illustrate an exemplary electroencephalogram (EEG) signal, recorded from an electrode overlying an epileptogenic focus, as a patient transitions through the various stages of an epileptic seizure. More specifically, FIG. 1(a) illustrates a time sequence of the EEG signal during the preictal stage, which represents the period of time preceding seizure onset. FIG. 1(b) illustrates a time sequence of the EEG signal during the transition period between the preictal stage and the ictal stage, which include seizure onset. It follows that FIG. 1(c) then reflects the EEG signal during the ictal stage, that is within the epileptic seizure, where the ictal stage begins at seizure onset and lasts until the seizure ends. FIG. 1(d), like FIG. 1(b), covers a transitional period. In this case, FIG. 1(d) illustrates a time sequence of the EEG signal during the transition from the ictal stage to the postictal stage, and includes the seizure's end. FIG. 1(e) then illustrates the EEG signal during the postictal stage, where the postictal stage covers the time period immediately following the end of the seizure.

As stated, the preictal stage represents a period of time preceding seizure onset. More importantly, the preictal stage represents a time period during which the brain undergoes a dynamic transition from a state of spatio-temporal chaos to a state of spatial order and reduced temporal chaos. Although it will be explained in greater detail below, this dynamic transition during the preictal stage is characterized by dynamic entrainment of spatio-temporal responses associated with various cortical sites. More particularly, the dynamic entrainment of the spatio-temporal responses at these various cortical sites can be further characterized by:

(1) the progressive convergence (i.e., entrainment) of the maximum Lyapunov exponent values (i.e., $L_{MAX}$) corresponding to each of the various, aforementioned cortical sites, where $L_{MAX}$ provides a measure of chaoticity associated with the spatio-temporal response of a corresponding cortical site; and (2) the progressive phase locking (i.e., phase entrainment) of the $L_{MAX}$ profiles associated with the various cortical sites.

It will be understood, however, that other measures of dynamic entrainment of the chaoticity profiles may be applied (e.g., among first, second or higher order derivatives of the Lyapunov exponent profiles).

As one skilled in the art will readily appreciate, an EEG signal, such as any of the EEG signals depicted in FIGS. 1(a-e), is a time series signal that represents a temporal response associated with the spatio-temporal interactions of a particular portion of the brain where the corresponding electrode happens to be located. Since, the brain is a complex, multidimensional system, EEG signals, and other known equivalents, do not and cannot visibly reflect the true spatio-temporal characteristics exhibited by the brain. Thus, traditional linear and nonlinear methods of processing EEG signals for the purpose of providing seizure prediction and/or warning have proven to be generally ineffective as the critical spatio-temporal characteristics exhibited by the brain during the preictal stage cannot be detected from EEG signals alone. Yet, these critical spatio-temporal characteristics exist long before seizure onset, in some cases, days before seizure onset. As such, these spatio-temporal characteristics exhibited by the brain during the preictal stage are essential to any true seizure prediction scheme.

Figure 2:
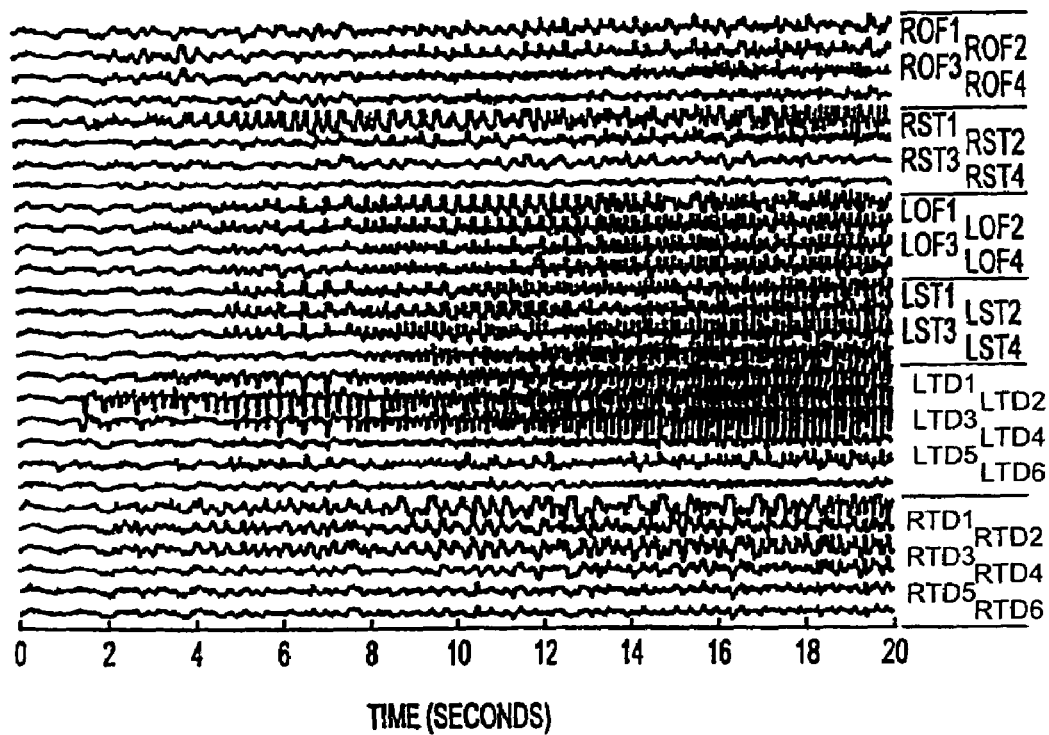
FIG. 2 illustrates a typical, continuous multichannel EEG segment prior to and during seizure onset.

To better illustrate the deficiency of EEG signals, FIG. 2 shows a 20 second EEG segment covering the onset of a left temporal lobe seizure. The EEG segment of FIG. 2 was recorded from 12 bilaterally placed hippocampal depth electrodes (i.e., electrodes LTD1-LTD6 and RTD1-RTD6), 8 subdural temporal electrodes (i.e., electrodes RST1-RST4 and LST1-LST4), and 8 subdural orbitofrontal electrodes (i.e., electrodes ROF1-ROF4 and LOF1-LOF4). Seizure onset begins approximately 1.5 seconds into the EEG segment as a series of high amplitude, sharp and slow wave complexes in the left depth electrodes, particularly in LTD1-LTD3, though most prominently in LTD2. Within a matter of seconds, the seizure spreads to right subdural temporal electrode RST1, and then to the right depth electrodes RTD1-RTD3. Of particular importance is the fact that the EEG signals appear normal prior to seizure onset approximately 1.5 seconds into the EEG segment.

The present invention involves a technique that is capable of providing an early, impending seizure warning (ISW). The present invention provides the early ISW by focusing on the aforementioned spatio-temporal changes that occur during the preictal stage. Moreover, the present invention provides this capability even though EEG signals do not manifest any indication of an impending seizure during the preictal stage, as illustrated in FIG. 2. However, in addition to providing an ISW, the present invention is also capable of providing a seizure susceptibility period detection (SSPD), that is, the presence of abnormal brain activity long before the occurrence of a seizure, for example, during an interictal period days before a seizure. Furthermore, the present invention is capable of providing a time to impending seizure prediction (TISP), wherein the TISP reflects an amount of time that is expected to elapse before seizure onset.

Figure 3A:
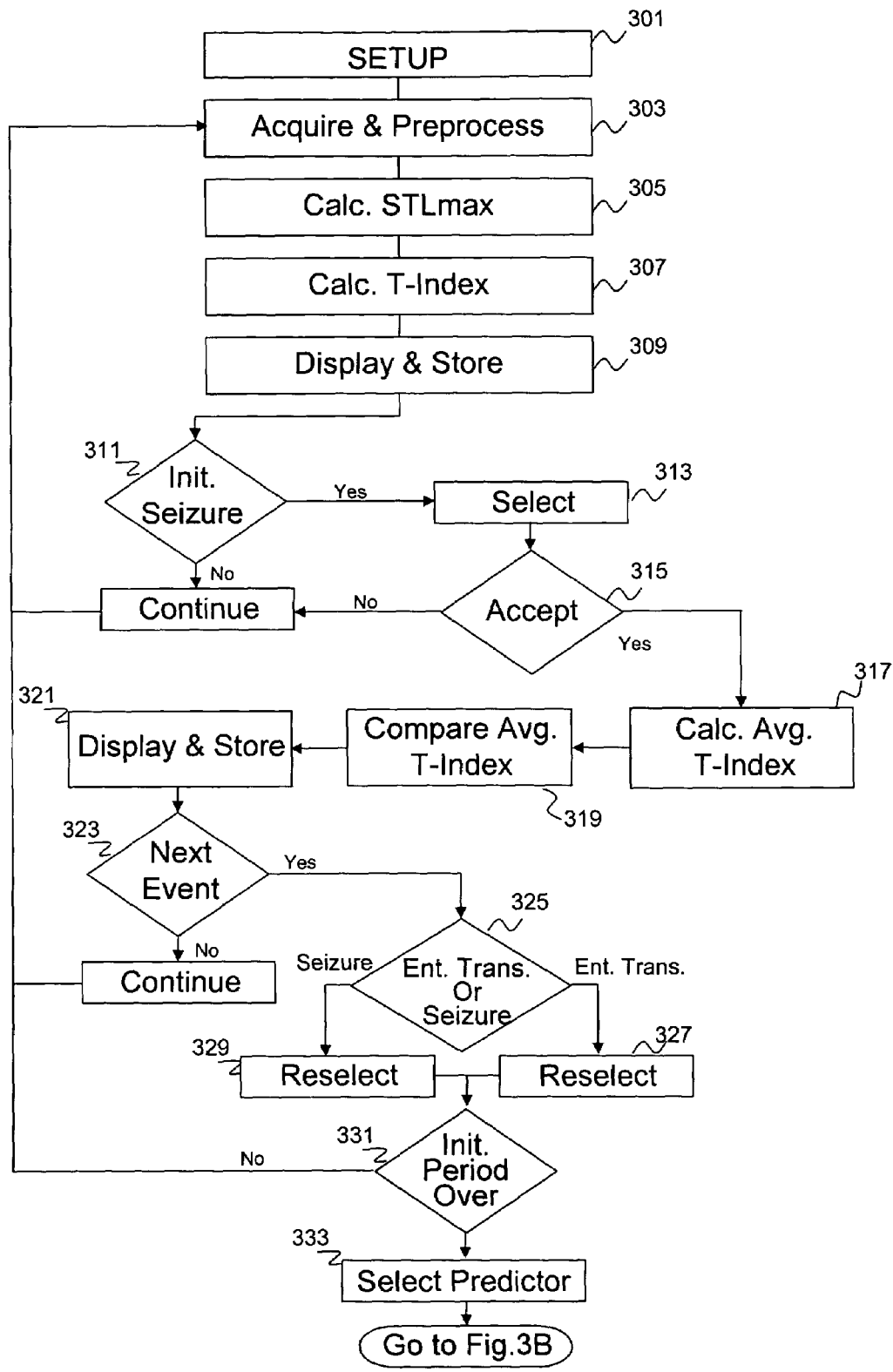
FIGS. 3A-3C are flowcharts depicting techniques for providing early ISW, SSPD and TISP in accordance with exemplary embodiments of the present invention.
Figure 3B:
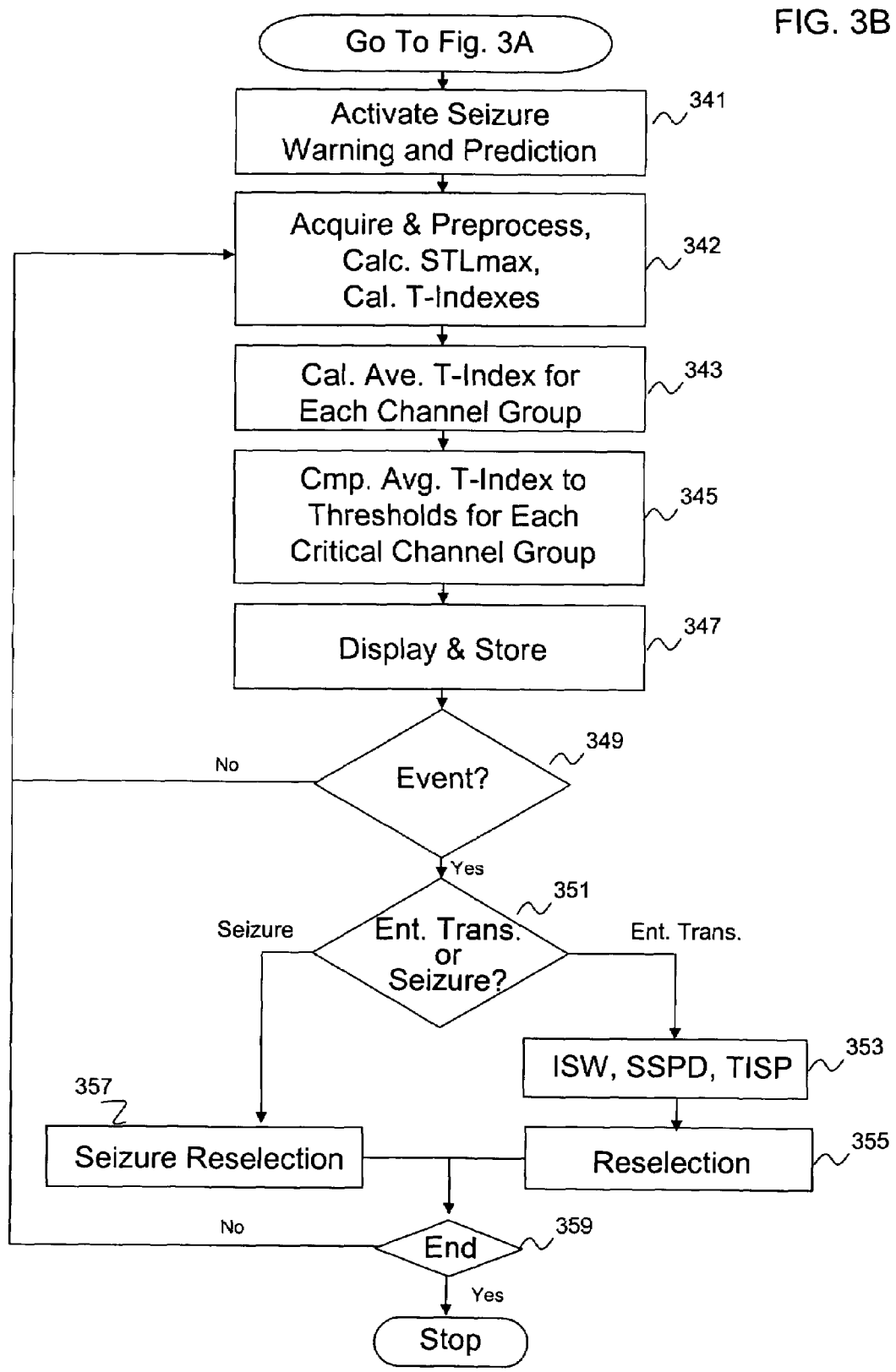

One skilled in the art will appreciate that the present invention has both clinical and non-clinical applicability. FIGS. 3A and 3B provide flowcharts illustrating a preferred embodiment of a method that is more likely to be employed in a clinical application. As shown, the method includes an initialization period. The primary objective of the initialization period is to establish a refined set of critical channels. After the initialization period, the statistical values (e.g., the T-index values) associated with the critical channels are continuously analyzed for the purpose of issuing ISWs, SSPDs and TISPs. This will be explained in greater detail below.

One skilled in the art will also appreciate the fact that the method illustrated in FIGS. 3A and 3B is a computer-based method. The same is also true of the method illustrated in FIG. 3C. As such, it will be understood that these methods will be an integral part of a larger, computer-based system, and primarily implemented in software, firmware or a combination of both. For ease of discussion, the software, firmware or combination thereof will be referred to herein as the "seizure warning and prediction algorithm" or simply, the "algorithm".

Looking now at the individual steps associated with the method of FIGS. 3A and 3B, step 301 represents a setup procedure. During this setup procedure, the clinician is given the opportunity to select or define various parameters, parameter values and threshold levels. For example, it is at this point that the clinician may define the number of electrodes to be used, as well as the location of each electrode. It will be understood that a number of electrode profiles may be stored in a memory that is part of, or associated with, the computer-based system. The user may then select and/or modify one of these profiles through interaction with a customized user interface, preferably a graphical user interface (GUI), which would also be part of, or associated with, the computer-based system.

Also during setup step 301, the clinician may be given the option of selecting, from a list of possible choices, the parameter that is to be used for measuring the level of divergence (i.e., chaoticity) of each channel's spatio-temporal response. In a preferred embodiment, the parameter to be used for this purpose is $L_{MAX}$, or the "short-term" equivalent thereof, $STL_{MAX}$. Similarly, the clinician may be given the option of selecting, from a list of choices, the statistical test to be used in determining the correlation (entrainment) level of the various channels. In a preferred embodiment, the statistical test used is the T-test, where the values produced as a result of applying a T-test are referred to herein as T-index values. How the $STL_{MAX}$ and T-index values are specifically used in the method of FIGS. 3A and 3B will be evident from the discussion herein below.

In addition to selecting certain desired parameters, the clinician may, during setup step 301, define the value of various thresholds. One such threshold is referred to herein as the disentrainment threshold $T_D$, where $T_D$ represents a T-index value, above which a corresponding group of channels is considered significantly and statistically disentrained. Another threshold is referred to herein as the entrainment threshold $T_E$, where $T_E$ represents a T-index value, below which a corresponding group of channels is considered sufficiently and statistically entrained. $T_{DIFF}$ is a value that represents the distance or difference between $T_D$ and $T_E$, where $T_D$ and/or $T_E$ may be adaptively changed with any change in the patient's state according to the T-index values. The relevance of these thresholds will become more evident from the discussion below.

Still other parameters and/or parameter values the clinician may select or define during setup step 301 include the number of channel groups (G), into which critical channels are assigned, and the number of critical channels (K) that can be assigned to a particular critical channel group. Once again, the relevance of the number of critical channel groups (G) and the number of channels per channel group (K) will be evident from the discussion below.

It should be noted that some parameters defined by the clinician during setup step 301 may be fixed, while others may be adaptive. A fixed parameter is a parameter that has a value which remains constant. An adaptive parameter is one that has a value which may automatically change over time depending upon one or more factors. By way of example, $T_{DIFF}$ represents a difference in correlation level between a level reflecting entrainment and a level reflecting disentrainment. If, during setup step 301, the clinician assigns values to $T_E$ or $T_D$ such that the value of $T_{DIFF}$ is too small, the result may be an unacceptably large number of false warnings (i.e., an ISW that is not followed by an actual seizure). If $T_{DIFF}$ is too large, the result may be an unacceptably large number of failed warnings (i.e., a failure to generate an ISW prior to an actual seizure). If, however, $T_E$ and/or $T_D$ are adaptable, their values may be incrementally adjusted by the algorithm until the number of failed and/or false warnings is acceptable.

Following setup step 301, the algorithm begins acquiring electrical or electromagnetic signals generated by the brain, as indicated by step 303. In a preferred embodiment, each of these signals corresponds to a single EEG channel, as explained above. Each signal is pre-processed. Pre-processing would typically include signal amplification, filtering and digitization. Each digitized signal is sampled, and for each, a sequence of phase space portraits is generated, where each phase space portrait is based on samples falling in a corresponding time window called an epoch.

For each channel, and for each of the sequential phase space portraits associated with a given channel, $STL_{MAX}$ values are computed based on adjacent trajectories in the phase space, where the $STL_{MAX}$ values associated with a phase space portrait of a given channel reflect the rate of divergence or choaticity level of the spatio-temporal signal corresponding to that channel. Average $STL_{MAX}$ values are then computed, where average $STL_{MAX}$ represents an average rate of divergence based on a number of $STL_{MAX}$ values falling within a "sliding" time window. The computation of $STL_{MAX}$ and average $STL_{MAX}$ is explained in greater detail below.

The average $STL_{MAX}$ values associated with a phase space portrait of a given channel are then compared to the average $STL_{MAX}$ values associated with a corresponding phase space portrait for each of the other channels. In a preferred embodiment of the present invention, the comparisons are achieved by applying a T-statistic, which takes into consideration the standard deviation of the differences between two channels in a "sliding" time window. As stated, this results in a series of statistical values, or T-index values, for each pair of channels, where the T-index values associated with a given channel pair reflect a level of correlation between the spatio-temporal responses of the two channels that make up the channel pair. The calculation of the T-index values for each channel pair is shown in step 307.

In a preferred embodiment, the algorithm continues to execute or perform steps 303-307 unless and until the entire process is terminated (e.g., by ending the EEG recording or external command from the operator). Accordingly, the algorithm will continue to acquire and process the electrical or electromagnetic signals associated with each channel, as set forth above. Further in accordance with a preferred embodiment, and in accordance with well established techniques, the algorithm will, if desired, display through the GUI a graphical representation of various data, including the electrical signals associated with each of or a selected number of channels, the $STL_{MAX}$ values for each of or a selected number of channels, and the T-index values for each of or a selected number of channel groups comprised of the critical channels, as shown in step 309. In addition, the algorithm may store this data in one or more appropriate data files, for future display, reference or analysis.

The electrical or electromagnetic signals, as stated, continue to be acquired and processed in accordance with the "NO" path out of decision step 311 until the patient experiences a first seizure. After a first seizure, as illustrated by the "YES" path out of decision step 311, the algorithm makes an initial critical channel selection, as illustrated in step 313. What this involves and how this is achieved will be described in greater detail below.

The seizure, of course, may be detected using any of a number of techniques. For example, the seizure may be detected by the clinician, who does so by physically observing the behavior of the patient. Alternatively, the seizure may be detected by the algorithm, which may do so by detecting a rapid decrease in a number of T-index values. As stated in U.S. Pat. No. 6,304,775, a seizure may also be detected by observing certain EEG signal manifestations indicative of a seizure. Other methods of seizure detection may be employed.

If a seizure is detected, the algorithm will, in accordance with a preferred embodiment of the present invention, mark the occurrence of the seizure, for example, by setting a status flag. Also, it will store seizure onset time in memory. The algorithm may set the status flag and store seizure onset time automatically if the algorithm itself detects the seizure. The algorithm may set the flag and store seizure onset time in response to an action taken by the clinician, where it is the clinician that detects the seizure. Regardless, it is the setting of the status flag that causes the algorithm to make the initial critical channel selection, as indicated in step 313.

In general, the initial selection of critical channels, in accordance with step 313, involves computing an average T-index value for each group of channels for each of a number of predictors, where a predictor is a specific number of critical channel groups (G) in combination with a specific number of channels per channel group (K), given a total number of channels (N). Typically, G will be in the range of 1-5 and K will be in the range of 3-6. When G ranges from 1-5 and K ranges from 3-6, there are 20 possible predictors: $G_1K_3, G_2K_3, G_3K_3 \ldots G_5K_6$. For each predictor $G_xK_y$, the algorithm considers each and every possible combination of "y" channels given a total number of channels N. For example, consider the predictor $G_3K_5$, where there are 30 total channels (N=30). For this predictor, $G_3K_5$, there are 142,506 different ways to group the 30 channels into groups of 5 channels each. A subset of 5 channels may belong to more than one group. For each of these 142,506 channel groups, and for each group of channels for each of the other predictors, the algorithm will compute an average T-index value. The average T-index value for each group, for each predictor $G_xK_y$, is computed based on the T-index values associated with the channel pairs that make up each corresponding group. It should be noted that the algorithm relies on a limited amount of data, for example, the T-index values within a 10 minute time window preceding, not necessarily immediately preceeding seizure onset, and the T-index values within a 10 minute time window following, not necessarily immediately following seizure onset. The algorithm then determines the most relevant channel groups for each predictor. This determination is based on the aforementioned two sets of T-index values (i.e., the 10 minutes preceding and 10 minutes following seizure onset) in each group, where the selected channel groups exhibiting the lowest average T-index values prior to seizure onset in combination with the condition that the average T-index values represent disentrainment following seizure onset. The "x" selected groups, for some or all of the predictors $G_xK_y$, exhibiting the most relevant behavior are identified as critical channel groups. For the predictor $G_3K_5$, the three (x=3) most relevant channel groups are identified as critical channel groups. The optimal predictor(s) $G_xK_yOpt_N$ will then be identified based on the prediction performance during the initialization period (i.e., 311-331).

After the initial critical channel selection, the clinician has an opportunity to accept or reject the selection, in accordance with decision step 315. If the clinician decides to reject the initial selection, in accordance with the "NO" path out decision step 315, the algorithm continues to acquire, process, display and store data until a subsequent seizure occurs followed by an acceptable critical channel selection. The clinician may decide to reject the initial selection for any number of reasons. One such reason is the clinician determines that the seizure was not typical. Consequently, the spatio-temporal response of the channels may not be indicative of a typical seizure.

After the initial seizure and after an acceptable critical channel selection, as illustrated by the "YES" path out of decision step 315, the algorithm continues calculating average T-index values for each channel group for each predictor $G_xK_y$, as shown in step 317. Then, per step 319, the algorithm takes the average T-index values associated with each critical channel group, for each predictor, and compares the average T-index values to one or more of the threshold values defined by the clinician during setup step 301 (e.g., $T_D$ and $T_E$). In a preferred embodiment, the algorithm also computes for each critical channel group a change in average T-index value, which is then compared to $T_{DIFF}$. It is anticipated that $T_D$ will be set in the range of 5-8, $T_E$ in the range of 3 or less. $T_{DIFF}$ may be used as a single independent parameter in the range of 2-7. In a preferred embodiment, the optimal thresholds are determined during the initialization period (i.e., 311-331). It should be noted that the optimal threshold values may be predictor dependent. That is, the optimal threshold value may be different for different predictors $G_xK_y$.

In this invention, a prediction or warning is declared when a preictal entrainment transition is observed in the T-index profiles of one or more critical channel groups for one or more predictors $G_xK_y$. As transition depends on the value of $T_E$ and $T_D$, determining the value of $T_E$ and $T_D$ is very important. In a preferred embodiment, the values are adaptively adjusted based on the state of the patient. For example, the value of $T_D$ may be set equal to the maximum T-index value in a previous time interval (e.g., a 20 minute time interval). The value of $T_E$ is then determined as a function of $T_D$ less a preset distance $T_{DIFF}$. An entrainment transition is observed if an average T-index profile exceeds $T_D$ and then subsequently drops below $T_E$.

As in step 309, step 321 illustrates that the algorithm is capable of continuously displaying, for all or a selected number of critical channel groups, the average T-index value and the average T-index value compared to one or more of the aforementioned threshold values. FIG. 13 illustrates a real time display of recorded EEG signals, the corresponding $STL_{MAX}$ values or profiles and the average T-index profiles for three selected critical channel groups. This continues as the algorithm awaits the occurrence of a next seizure-related event, in accordance with decision step 323, where a seizure-related event includes a seizure or an entrainment transition event. If the algorithm determines that no seizure nor an entrainment transition event are occurring, the algorithm continues to acquire, process, display and store data, as described above, and calculate and compare average T-index values for each predictor, in accordance with the "NO" path out of decision step 323. If, on the other hand, the algorithm determines, in accordance with the "YES" path out of decision step 323, that a seizure-related event has occurred, the algorithm will reselect and update the critical channel groups for some or all of the predictors $G_xK_y$ depending upon whether the seizure-related event was a seizure or an entrainment transition, as determined in accordance with decision step 325.

As stated, the algorithm may determine that a seizure has or is occurring in any one of a number of ways. In contrast, the algorithm may determine that an entrainment transition event has occurred. The algorithm may determine that a new seizure event has occurred by detecting conditions that would otherwise cause the algorithm to issue an ISW. Thus, if for any predictor $G_xK_y$, the average T-index value corresponding to one or more critical channel groups drops below $T_E$ for a predefined, statistically significant period of time, the algorithm will establish that an entrainment transition event has occurred. The conditions upon which the issuance of an ISW is predicated will be explained in detail below.

If the algorithm determines that the seizure-related event is a seizure, in accordance with the "SEIZURE" path out of decision step 325, the algorithm reselects the critical channel groups for all or some of the predictors $G_xK_y$. As in step 313, the reselection is achieved based on average T-index values corresponding to each and every possible channel group for all or some of the predictors $G_xK_y$. Again, in accordance with a preferred embodiment, the algorithm only relies on average T-index values in a predefined time window preceding (e.g., a 10 minute time window not necessarily immediately preceding) seizure onset, and average T-index values in a predefined time window following (e.g., a 10 minute time window not necessarily immediately following) seizure onset. It will be understood that the algorithm may, in addition to relying on average T-index values associated with the present seizure, rely on average T-index values associated with prior seizure-related events. If so, it is preferable to apply appropriate weighting factors to the data, such that the average T-index values associated with the present seizure have a more significant influence on the reselection of critical channels than T-index values associated with previous seizures and/or near-seizure events.

If, instead, the algorithm determines that the seizure-related event is an entrainment transition event, in accordance with the "entrainment transition" path out of decision step 325, the algorithm reselects the critical channel groups, but only for the predictor or predictors whose critical channels exhibited behavior indicative of an entrainment transition event. In a preferred embodiment, the reselection of critical channels associated with an entrainment transition event takes into consideration the average T-index values, for each and every possible channel group, in a predefined time window (e.g., a 20 minute time window) preceding the determination that an entrainment transition event has occurred or a window mostly preceding but with an overlap after the time the transition event occurred. Once again, average T-index values associated with prior seizure-related events may factor into the reselection process, where appropriate weighting factors are assigned such that the average T-index values associated with the present entrainment transition event are given more deference in the reselection process than the average T-index values associated with prior events.

When the method illustrated in FIG. 3A is first employed, for instance, when it is used in conjunction with a new patient, there is an initialization period. The primary purpose of the initialization period is, as previously explained, to provide a period during which the algorithm may refine and establish the optimal predictor(s) to enable the selection of critical channels whose behavior is subsequently relied upon for issuing seizure warnings and predictions. Accordingly, as shown in step 331, the algorithm periodically checks for some indication signaling the end of the initialization period. Such an indication may take the form of an electrical signal generated in response to a clinician's input, where the clinician has determined that the optimal predictor(s) for the critical channel selection is now adequately stable and refined. Alternatively, the clinician may be given the option during the setup step 301 to define the initialization period in terms of a predefined number of seizure-related events (S). If the algorithm makes no such determination, that is, the algorithm determines the initialization period is not over, in accordance with the "NO" path out of decision step 331, the algorithm continues to acquire, process, display and store spatio-temporal response data, as described, calculate and compare average T-index values, and await a next seizure-related event. If, however, the algorithm determines that the initialization period is over, in accordance with the "YES" path out of decision step 331, the end of the initialization period is marked by the selection of a particular predictor or predictors $G_xK_y$ and the identification of the critical channels that make up each of the x number of critical channel groups associated with selected predictor $G_xK_y$, as illustrated by step 333. If, for example, step 333 results in the selection of predictor $G_3K_5$, three critical channel groups are identified, each containing five critical channels, where these three groups of five critical channels exhibited behavior most indicative of the seizure-related events during the initialization period. The process then transitions over to a post-initialization period as illustrated by the method of FIG. 3B.

FIG. 3B is, more specifically, a flowchart depicting a method of issuing an ISW, SSPD and/or TISP after the initialization period is over. It will be noted that generating an ISW, SSPD and/or TISP during the initialization period is certainly feasible by using default or clinician selected predictor(s) with corresponding parameters; however, in accordance with the embodiment illustrated in FIGS. 3A and 3B, that is not the case. Consequently, the first step in the method of FIG. 3B is step 341, wherein the algorithm activates the seizure warning and prediction features. These features may be automatically activated by setting a software "switch", by setting a status flag, or by any similar process that causes, thereafter, the algorithm to issue an ISW, SSPD and/or TISP under the appropriate conditions. In step 342, the method will acquire and preprocess the electrical or electromagnetic signals, calculate the $STL_{MAX}$ values, and calculate T-index values.

In step 343, the algorithm calculates the average T-index value for all possible channel groups associated with the predictor selected during step 333. However, in accordance with step 345, the algorithm only compares the average T-index values associated with the critical channel groups to the aforementioned threshold values, where the generation of an ISW, SSPD and/or TISP will be based on the result of these comparisons. Again, the data associated with these calculations and comparisons may be displayed through the GUI and stored per step 347.

The algorithm will continue to execute steps 343-347 and, simultaneously, monitor conditions for indications of a next seizure-related event, as shown by decision steps 349, in much the same way that the algorithm did so per step 323 in FIG. 3A. If, as shown by the "SEIZURE" path out of decision step 351, the algorithm determines that a seizure is occurring, the algorithm stores the seizure onset time and, thereafter, reselects the critical channel groups corresponding to the predictor selected during step 333. Again, in a preferred embodiment, reselection is based on an analysis of the average T-index values of all possible channel groups associated with the selected predictor over a predefined time window (e.g., a 10 minute time window) preceding seizure onset time and the average T-index values of all possible channel groups associated with the selected predictor over a predefined time window (e.g., a 10 minute time window) following the seizure onset time. The algorithm repeats this process, in accordance with the "NO" path out of decision step 359, until terminated per the "YES" path out of decision step 359.

If the algorithm determines that the constraints necessary to issue a warning and/or prediction have been met, in accordance with the "WARNING" path out of decision step 351, the algorithm generates an ISW, SSPD or TISP, as shown in step 353. The algorithm then reselects the critical channel groups of the predictor(s) per step 355, wherein the reselection is, in this instance, based only on the average T-index values of all channel groups associated with the selected predictor over a predefined time period (e.g., a 20 minute time window) preceding or mostly preceding the time of the entrainment transition event. A more detailed discussion of ISWs, SSPDs and TISPs is provided below. Again, the algorithm continues to repeat the process until terminated in accordance with the "YES" path out of decision step 359.

It is important to note that in accordance with a preferred embodiment of the present invention, the algorithm continues to reselect and update the critical channel groups for the predictor(s) after each seizure-related event, that is, after each seizure and after each entrainment transition, per steps 355 and 357. Thus, it can be said that the critical channel selection process is iterative and adaptive before and after the initialization period. The reason for doing so is based on observations that seizures are resetting mechanisms of the brain's spatio-temporal entrainment with the epileptogenic focus, which is the precursor of an impending seizure. See J. C. Sackellares et al. "*Epileptic Seizures as Neural Resetting Mechanisms,*" Epilepsia, vol. 38, p. 189, 1997, see also, L. D. Iasemidis et al., "*Dynamical Resetting of Human Brain at Epileptic Seizures: Application of Nonlinear Dynamics and Global Optimization Techniques,*" IEEE Transactions on Biomedical Engineering, in press 2003. It is therefore important to continuously update the predictor(s) with the critical channels, from one seizure-related event to the next because the brain does not necessarily reset itself completely after each seizure and, as a result, the spatio-temporal characteristics associated with any channel may change over time. Accordingly, a channel previously identified as belonging to a critical channel group may now exhibit a spatio-temporal response that warrants its disassociation from that groups. Likewise, a channel that was not previously identified as belonging to a critical channel group may now exhibit behavior that warrants its inclusion. This iterative and adaptive refinement of the critical channels reduces the number of false warnings and increases the sensitivity to seizure detection and prediction.

Figure 3C:
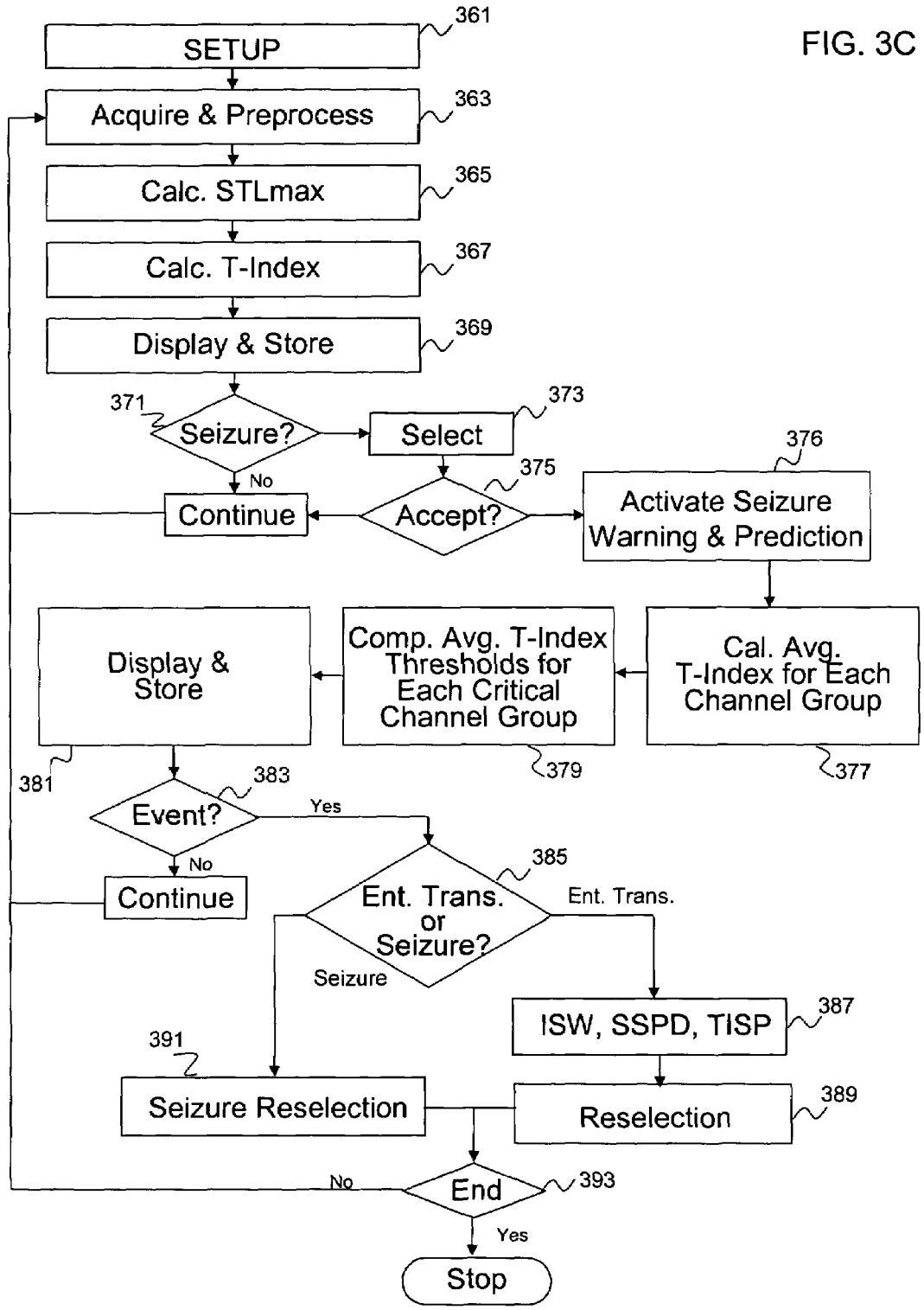

FIG. 3C is a flowchart depicting a method for generating an ISW, SSPD and/or TISP in a non-clinical application. As is readily apparent, the method depicted in FIG. 3C is substantially similar to the method depicted in FIG. 3A. The electrical or electromagnetic signals continue to be acquired and processed in accordance with the "NO" path out of decision step 371 until the patient experiences a seizure. After a seizure, as illustrated by the "YES" path out of decision step 371, the algorithm makes a critical channel selection, as illustrated in step 373. One difference, however, is that the non-clinical method depicted in FIG. 3C does not employ a distinct initialization period. As such, there is no time period during which the algorithm selects a particular predictor $G_x K_y$. Instead, the clinician may make this selection during setup step 361. Alternatively, the algorithm could provide a default selection. In addition, as there is no initialization period, the seizure warning and prediction features are activated, as illustrated in step 376, after the acceptance step 375 of the initial critical channel selection. Accordingly, the algorithm will issue an ISW, SSPD and/or TISP in accordance with the "YES" path out of decision step 383, the "WARNING" path out of decision step 385, and step 387 if it determines that the corresponding conditions for doing so have been met. Thereafter, the algorithm reselects the critical channel groups, as shown in step 389, in the same manner as described for step 355 of FIG. 3B. If, instead, the algorithm detects a seizure, in accordance with the "YES" path out of decision step 383 and the "SEIZURE" path out of decision step 385, the algorithm will thereafter reselect the critical channel groups as shown in step 391, in the same way the algorithm reselected the critical channel groups in step 357 of FIG. 3B. The algorithm repeats this process, in accordance with the "NO" path out of decision step 393, until terminated per the "YES" path out of decision step 393.

The methods depicted in FIGS. 3A-3C are intended to illustrate general procedures in accordance with exemplary embodiments of the present invention. The specific techniques, and alternatives thereto, used to implement the various steps will now be described in greater detail.

As illustrated in FIGS. 3A and 3C, steps 305 and 363, respectively, involve the acquisition of electrical or electromagnetic signals generated by the brain. In accordance with a preferred embodiment of the present invention, electrodes are used to record electrical potentials, where each electrode corresponds to a separate channel, and where recordings are made using differential amplifiers. In referential recordings, one of the electrodes is common to all channels. The electrodes are strategically placed so that the signal associated with each channel is derived from a particular anatomical site in the brain. Electrode placement may include, for example, surface locations, wherein an electrode is placed directly on a patient's scalp. Alternatively, subdural electrode arrays and/or depth electrodes are sometimes employed when it is necessary to obtain signals from intracranial locations. However, one skilled in the art will appreciate that the specific placement of the electrodes will depend upon the patient, as well as the application for which the signals are being recorded.

Figure 4A:
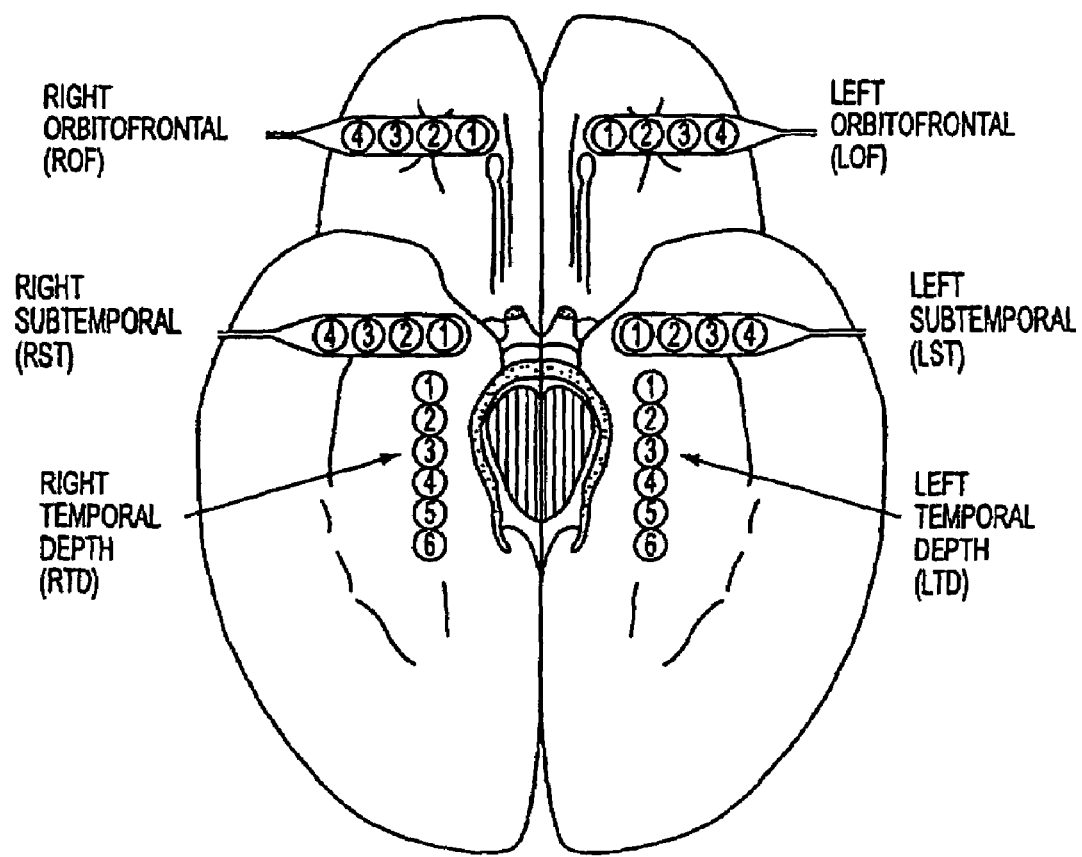
FIGS. 4A and 4B illustrate the placement and use of different electrodes and electrode configurations.
Figure 4B:
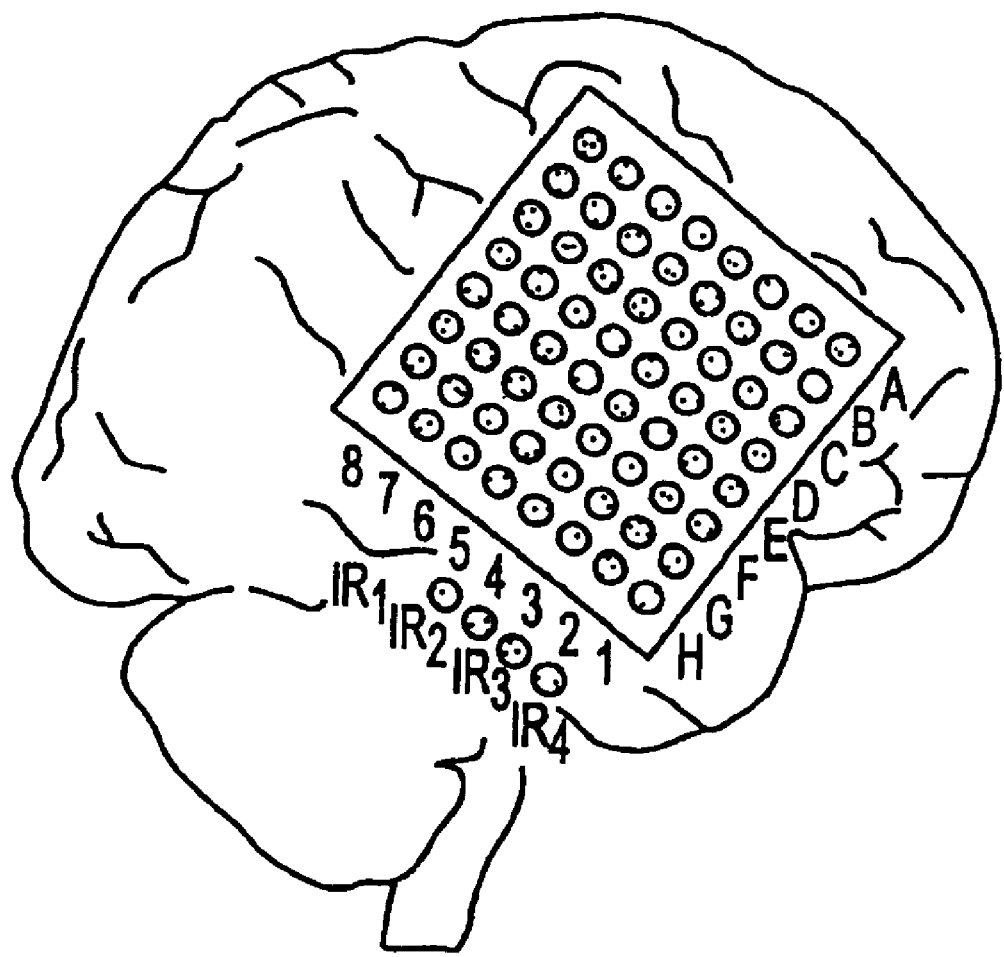

FIG. 4A provides a view from the inferior aspect of the brain and exemplary locations for a number of depth and subdural electrodes. As shown, the electrodes include six right temporal depth (RTD) electrodes and six left temporal depth (LTD) electrodes located along the anterior-posterior plane in the hippocampi. FIG. 4A also includes four right orbitofrontal (ROF), four left orbitofrontal (LOF), four right subtemporal (RST) and four left subtemporal (LST) subdural electrodes located beneath the orbitofrontal and subtemporal cortical surfaces. FIG. 4B illustrates the placement of and use of a subdural electrode array as well as a strip of electrodes on the inferior right temporal lobe.

In accordance with an alternative embodiment of the present invention, magneto-electroencephalography (MEG) may be employed to record the magnetic fields produced by the brain. With MEG, an array of sensors called superconducting quantum interference devices (SQUIDs) are used to detect and record the magnetic fields associated with the brain's internal current sources.

In yet another alternative embodiment, micro-electrodes may be implanted into the brain to measure the field potentials associated with one or just a few neurons. It will be understood that the use of micro-electrodes might be advantageous in very select applications, where, for example, it might be necessary to define with a high degree of accuracy the location of the epileptogenic focus prior to a surgical procedure.

Steps 303 and 363 in FIGS. 3A and 3C also involve pre-processing the signals associated with each channel. These pre-processing steps include, for example, signal amplification, filtering and digitization. In a preferred embodiment, filters, including a high pass filter with 0.1 to 1 Hz cutoff and a low pass filter with 70-200 Hz cutoff, are employed. Depending on the application and/or the signal recording environment, other filters may be employed. For instance, if the signals are being recorded in the vicinity of power lines or any electrical fixtures or appliances operating on a 60 Hz cycle, a 60 Hz notch filter or time varying digital filters may be employed. Pre-processing results in the generation of a digital time series for each channel.

Steps 303 and 363 further involve generating phase portraits, and in particular, p-dimensional phase space portraits for each channel, where p represents the number of dimensions necessary to properly embed a brain state. In a preferred embodiment of the present invention, the p-dimensional phase space portraits are generated as follows, where p is assumed to be at least seven (7) to capture the dynamic characteristics of the ictal state, which may be present during the preictal state. First, the digital signals associated with each channel are sampled over non-overlapping or overlapping sequential time segments, referred to herein as epochs. Each epoch may range in duration from approximately 5 seconds to approximately 24 seconds, depending upon signal characteristics such as frequency content, amplitude, dynamic properties (e.g., chaoticity or complexity) and stationarity. Generally, epoch length increases as stationarity increases. In an exemplary embodiment of the present invention, a signal may be sampled approximately 2000 times per epoch, where the epoch is approximately 10 seconds in duration.

The samples associated with each signal, taken during a given epoch, are then used to construct a phase space portrait for the corresponding channel. In a preferred embodiment of the present invention, the phase space portraits are constructed using a method called "The Method of Delays." The Method of Delays is well known in the art. A detailed discussion of this method with respect to analyzing dynamic, nonlinear systems can be found, for example, in Iasemidis et al., "*Phase Space Topography of the Electrocorticogram and the Lyapunov Exponent in Partial Seizures*", Brain Topogr., vol. 2, pp. 187-201 (1990). In general, a phase space portrait is constructed using the Method of Delays by independently treating each unique sequence of p consecutive sample values, separated by a time delay $\tau$, as a point to be plotted in the p-dimensional phase space. In an exemplary implementation of the present invention, $\tau$ equals 4 samples (20 msec).

Figure 5A:
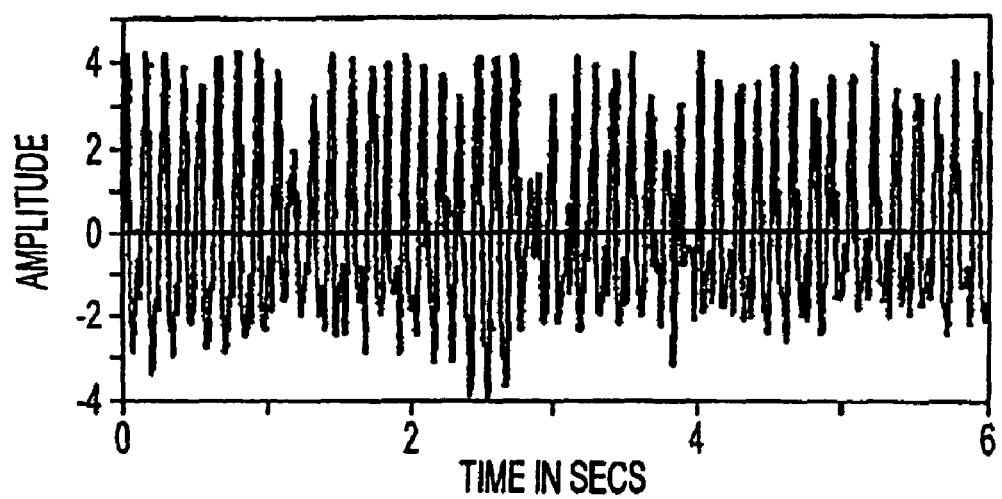
FIGS. 5A and 5B illustrate an EEG signal associated with a representative electrode channel over an epoch and the corresponding phase space portraits containing the attractor reconstructed from the EEG signal using the Method of Delays.
Figure 5B:
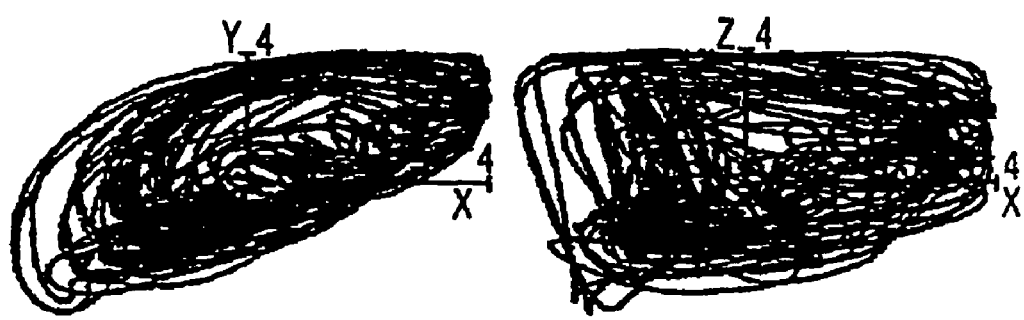
Figure 6:
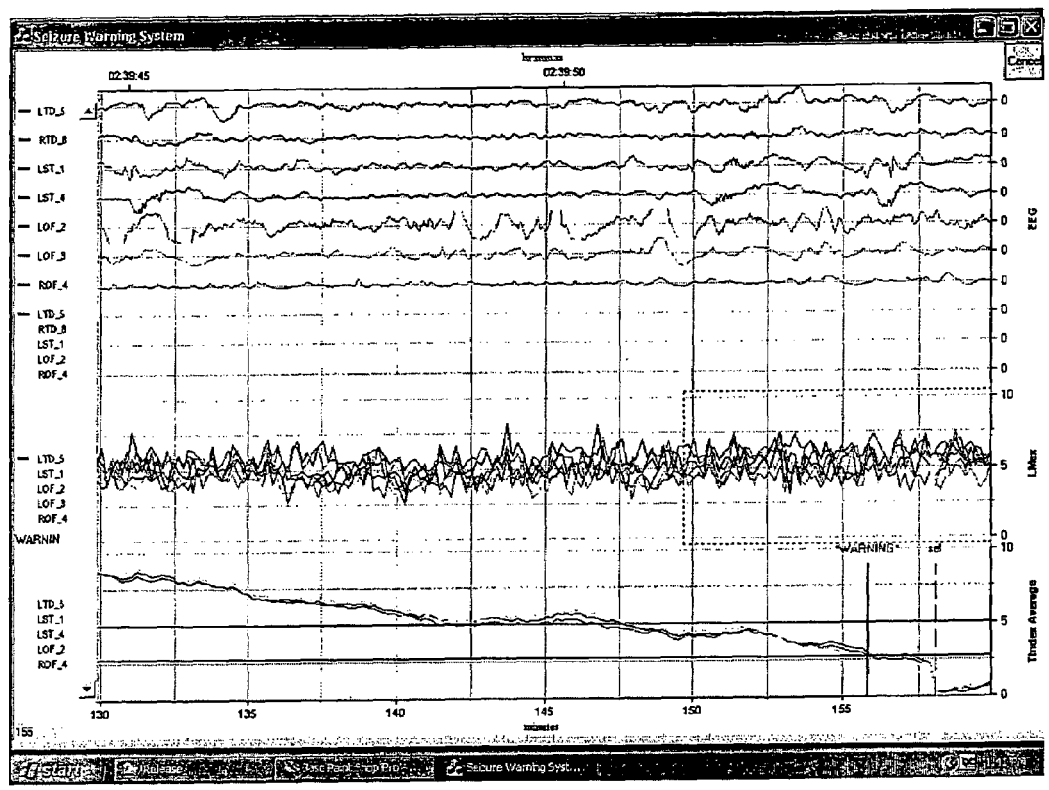
FIG. 6 is a real time display of recorded EEG signals, corresponding $STL_{max}$ values or profiles and average T-index values for selected critical channel groups.

FIG. 5A shows a 6 second epoch associated with an exemplary EEG signal at the onset of a seizure that originated in the left temporal cortex. FIG. 5B illustrates, from different perspectives, the corresponding phase space portrait, projected in three dimensions, for the exemplary EEG signal of FIG. 5A. The object appearing in the phase space portrait of FIG. 5B is called an "attractor". The attractor represents the region within the phase space in which the states of the system evolve and remain confined thereto until the structure of the system changes.

Steps 305 and 365 in FIGS. 3A and 3C, respectively, involve quantifying the chaoticity of the attractor associated with each channel. There are, of course, different techniques that can be used to accomplish this. However, in accordance with a preferred embodiment of the present invention, the chaoticity of each attractor is quantified using Lyapunov exponents, which represent the average rate of divergence (i.e., expansion or contraction) between point pairs of trajectories that are in close proximity to one another in the phase space. In multidimensional systems, the number of possible Lyapunov exponents is equal to the dimension (p) of the reconstructed state space. Therefore, quantifying the system's behavior may involve calculating sequences of one or more Lyapunov exponents. For instance, if the number of dimensions characterizing the state space is seven (7), then seven (7) different Lyapunov exponent sequences may be computed in quantifying the chaoticity associated with the system's behavior. However, to strike a balance between chaoticity measurement accuracy and signal processing efficiency, only the largest Lyapunov exponent (i.e., $L_{MAX}$) is used in accordance with a preferred embodiment of the present invention. Although one skilled in the art will readily appreciate that it may be desirable to utilize more than one Lyapunov exponent (i.e., Lyapunov exponents in addition to $L_{MAX}$) in order to optimize sensitivity and seizure prediction accuracy. For example, it may be desirable to use more than $L_{MAX}$ for cases where it is essential to predict seizure onset time with the highest possible degree of accuracy.

Further, in accordance with a preferred embodiment of the present invention, an $L_{MAX}$ value is ultimately derived for each epoch, thereby resulting in a sequence of $L_{MAX}$ values over time for each channel. This sequence of $L_{MAX}$ values (herein referred to as an $L_{MAX}$ profile) represents the chaoticity of the corresponding channel over time. A more complete explanation regarding the computation and utilization of Lyapunov exponents can be found, for example, in Wolf et al., "*Determining Lyapunov Exponents from a Time Series*," Physica D, vol. 16, pp. 285-317 (1985) and Eckmann et al., "*Lyapunov Exponents from Times Series*," Phys. Rev. A, vol. 34, pp. 4971-4972 (1986). In the Iasemidis et al., publication entitled "*Phase Space Topography of the Electrocorticogram and the Lyapunov Exponent in Partial Seizures*", a method for computing and utilizing short-term Lyapunov exponents (i.e., $STL_{MAX}$) is described, wherein the method takes into account the nonstationarity of the EEG data, a feature of paramount importance for the accurate estimation of $L_{MAX}$ from EEG in epileptic patients. The reason this feature is so important is the existence of excessive transients (e.g., epileptic spikes, fast or slow wave transients etc.) in the EEG from such patients.

Steps 307, 317 and 319 in FIG. 3A, 343 and 345 in FIG. 3B, and 367, 377 and 379 in FIG. 3C involve evaluating the entrainment of the $L_{MAX}$ profiles, or more specifically, $STL_{MAX}$ profiles. Evaluation may be achieved by calculating the average and standard deviation of the difference over consecutive $STL_{MAX}$ values falling within a "sliding" time window. The length of time associated with the "sliding" time windows is approximately 10 minutes (i.e., a span of approximately 60 epochs). The result is a sequence of average T-index 15 values over time for each channel group of the predictor. The data associated with these calculations may be displayed through the GUI and stored per step 309 in FIG. 3A, 347 in FIG. 3B and step 369 in FIG. 3C.

In general, step 307 in FIG. 3A and step 367 in FIG. 3C involve comparing the $STL_{MAX}$ profile associated with each channel to the $STL_{MAX}$ profile associated with each of the other channels to determine whether the corresponding pair of signals show signs of entrainment. For the purpose of the present invention, the term "entrain" refers to a correlation or convergence in amplitude and/or phase between measures of two signals that make up a channel pair. Although any number of statistical methods may be employed to quantify the degree of correlation between a pair of signals, a pair T-statistic is employed for this purpose in accordance with a preferred embodiment of the present invention.

By applying the pair T-statistic, a T-index is derived for each of a number of overlapping or non-overlapping "sliding" time windows for each channel pair, wherein the duration of a time window may vary from approximately 1 minute to 20 minutes. As already mentioned, in a preferred embodiment of the present invention, the duration of these "sliding" time windows is approximately 10 minutes. Optimally, the length of time associated with these time windows must capture, with sufficient resolution, and a minimum number of computations, the dynamic spatio-temporal transitions during the preictal stage. Since the preictal transitions are ultimately characterized by the progressive entrainment of $STL_{MAX}$ profiles associated with critical channel groups, it is the rate of entrainment between the $STL_{MAX}$ profiles and the level of statistical significance that determines the optimum length of these time windows.

Figure 7:
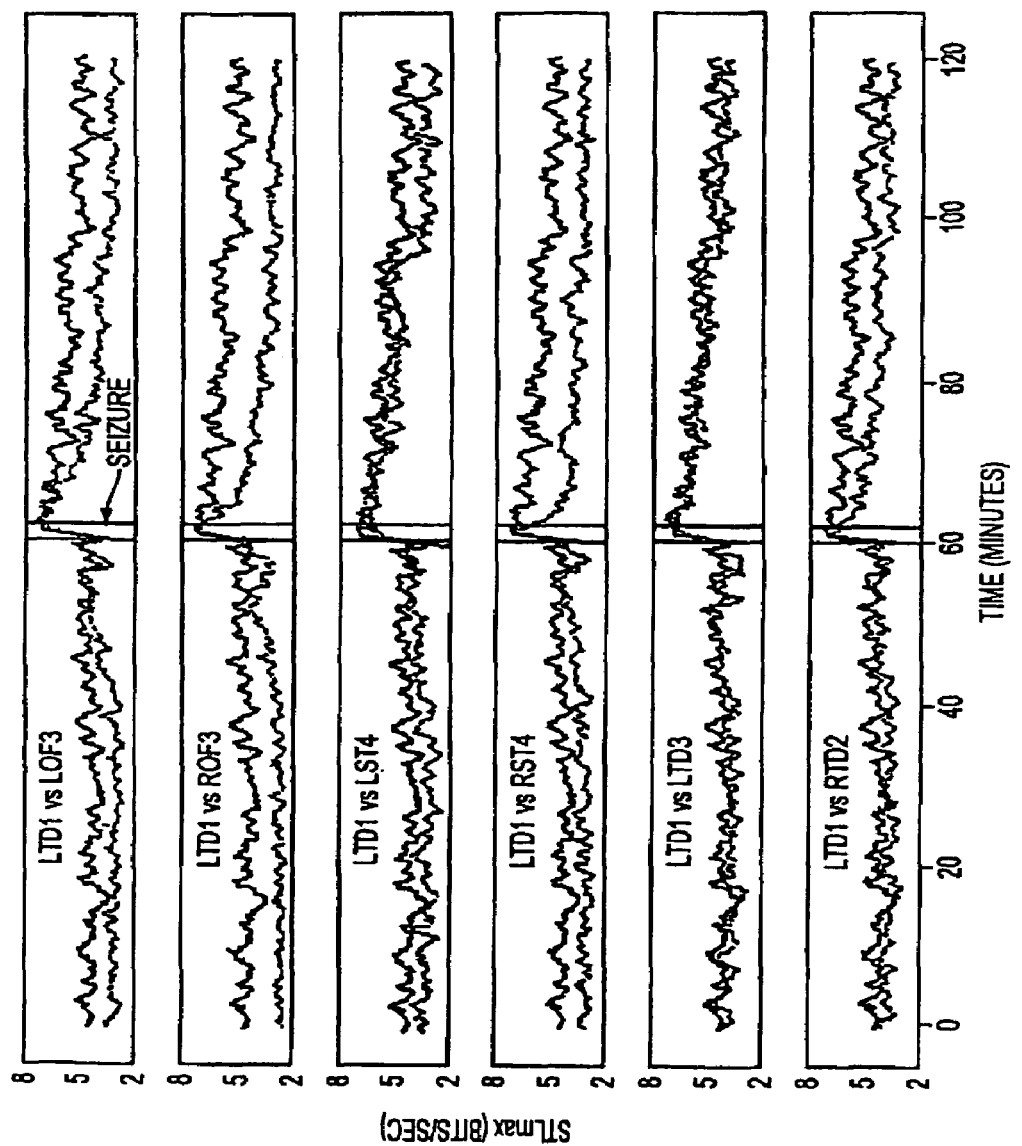
FIG. 7 illustrates the $L_{MAX}$ profiles associated with each of a representative number of channel pairs.

FIG. 7 illustrates a comparison between the $STL_{MAX}$ profiles associated with each of a representative number of channel pairs. More particularly, FIG. 7 shows a comparison between the $STL_{MAX}$ profile corresponding to a signal associated with a left temporal depth electrode LTD1 and the $STL_{MAX}$ profile associated with six other representative electrode sites. The six other representative electrode sites are a left orbitofrontal electrode LOF3, a right orbitofrontal electrode ROF3, a left subtemporal electrode LST4, a right subtemporal electrode RST4, a left temporal depth electrode LTD3 and a right temporal depth electrode RTD2. Although FIG. 7 only shows $STL_{MAX}$ profile comparisons for six representative channel pairs, in a preferred embodiment of the present invention, steps 307 and 367 in FIGS. 3A and 3C, respectively, involve $STL_{MAX}$ profile comparisons for all channel pairs. For example, if signals are being recorded at 20 different electrode sites, procedural step 307 would typically involve 190 Lmax profile comparisons, as there are 190 different channel pairs.

Figure 8:
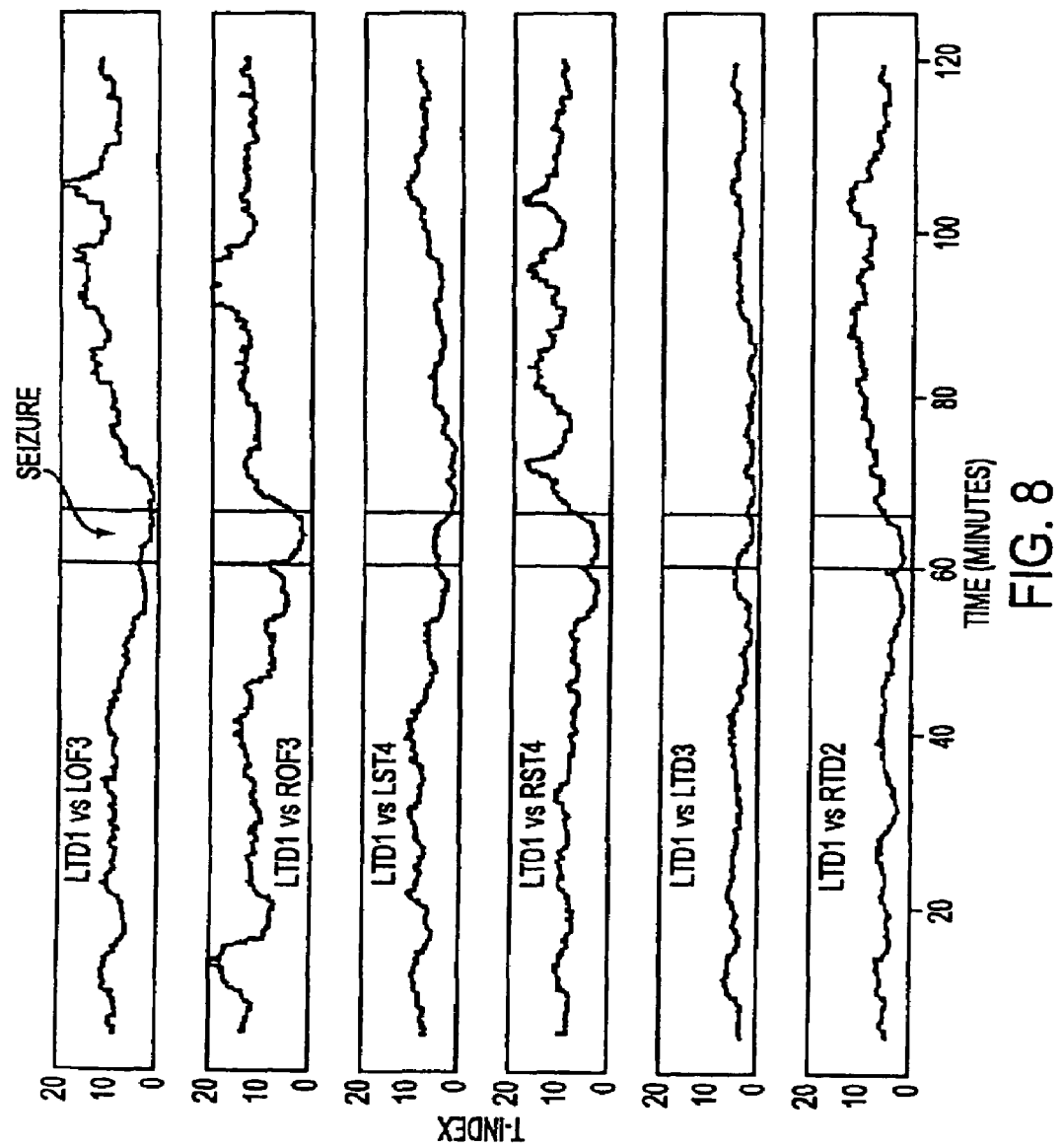
FIG. 8 illustrates a procedure for comparing $L_{MAX}$ profiles (e.g., estimations of T-index profiles) for the representative number of channel pairs shown in FIG. 7.

FIG. 8 illustrates the T-index profiles that correspond with the six channel pairs illustrated in FIG. 7. From the T-index profiles illustrated in FIG. 8, it is evident that the $STL_{MAX}$ profiles associated with each channel pair all progressively become entrained during the preictal stage (i.e., during the 0-60 minute time frame), while each channel pair becomes progressively disentrained during the postictal stage. However, the rate and degree at which the $STL_{MAX}$ profiles become entrained and disentrained vary. In FIG. 8, the channel pair associated with the electrode LTD1 and electrode LTD3 demonstrates a relatively high level of entrainment (i.e., relatively low T-index values), more so than the other five channel pairs. The channel pair associated with the electrode LTD1 and electrode RTD2 also shows a relatively high level of entrainment, particularly during the preictal stage. Although FIG. 8 only shows T-index values 60 minutes prior to and 60 minutes following seizure onset, the preictal period typically begins approximately 15 minutes to as much as 2 hours prior to seizure onset. However, it is extremely important to note that signs of entrainment, such as reduced T-index values, particularly those associated with critical channels, may be evident long before seizure onset. In fact, it is possible that critical channels will exhibit signs of an impending seizure days before an actual seizure.

Steps 313, 327 and 329 in FIG. 3A, 355 and 357 in FIG. 3B, and 373, 389 and 391 in FIG. 3C all involve the selection or reselection of critical channels, or more specifically, critical channel groups. In general, that portion of the algorithm which controls this section process ultimately seeks to identify those channel groups which are critical, given the constraints defined by the clinician. During the initialization period covered by the method steps in FIG. 3A, the algorithm seeks to identify critical channel groups for all predictor $G_xK_y$, as explained above. After the initialization period, as covered by the steps in FIG. 3B, and in accordance with the non-clinical method illustrated in FIG. 3C, the algorithm seeks to identify the critical channel groups associated with at least one selected predictor.

Steps 353 and 387 in FIGS. 3B and 3C, respectively, involve generating an ISW, SSPD and/or a TISP. The specific techniques employed to generate an ISW, SSPD and/or TISP, in accordance with these steps, will now be described in greater detail. The first of these features to be described is the early ISW feature. In general, an ISW is triggered when one or more critical channel groups associated with a selected predictor are highly disentrained (i.e., average T-index values above $T_D$) and then later they become entrained (i.e., average T-index values below $T_E$) for a statistically significant period of time. More specifically, an ISW is generated when the average T-index values associated with the one or more critical channel groups, previously above a disentrainment threshold, fall below a statistically significant entrainment threshold value for a statistically significant period of time. In a preferred embodiment, that threshold is $T_E$. Further in accordance with a preferred embodiment, the statistically significant period of time during which the average T-index value must remain below $T_E$ in order to trigger an ISW is typically set somewhere between 0 minutes and 1.5 hours. For example, an average T-index value less than $T_E$=2.09 for a period of time equal to 15 minutes equates to a 99 percent confidence level that the issuance of an ISW is a valid warning. Of course, it will be understood that the threshold value $T_E$ and the duration which the average T-index must remain below that threshold value may be adaptively adjusted to increase or decrease ISW sensitivity and reduce the incidence of false warnings (i.e., false positives) for any given patient, or reduce the incidence of failed warnings (i.e., false negatives).

The ISW may be implemented in any number of ways. For example, the ISW may involve audible warnings or visual warnings or a combination of both visual and audible warnings. In fact, the ISW may involve nothing more than the setting or resetting of an internal software variable or flag, wherein the setting or resetting of the variable or flag triggers a dependent event, such as the automatic delivery of anti-seizure medication. Accordingly, the specific implementation of the ISW will depend on the specific clinical or non-clinical application for which the present invention is being employed.

Figure 9:
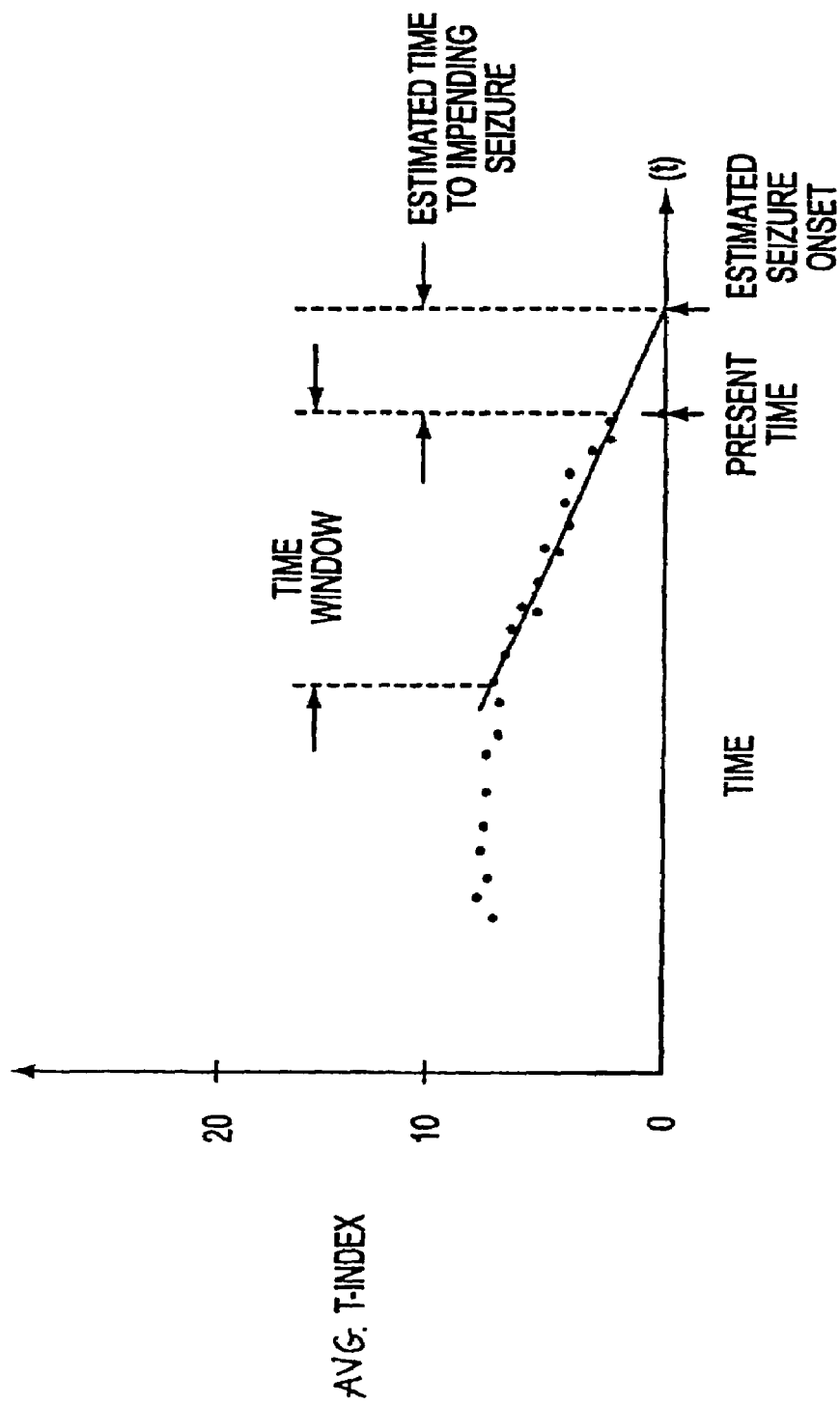
FIG. 9 illustrates the TISP feature in accordance with exemplary embodiments of the present invention.

The next feature is the TISP feature. Once the algorithm generates and ISW, the rate of entrainment, that is, the rate at which the $STL_{MAX}$ profiles associated with a critical channel group continue to converge, may be used to estimate the amount of time before seizure onset. In accordance with a preferred embodiment of the present invention, this is accomplished by continuously deriving, for each of the one or more critical channel groups, the slope of the corresponding, average T-index profile over a "sliding" time window, as illustrated in FIG. 9. The point at which the slope intercepts the time (t) axis represents an estimated seizure onset time. Therefore, the difference between the present time and the estimated seizure onset time, along the time (t) axis, represents the TISP. The length of the "sliding" time window may, once again, vary. Initially, it may be set to a relatively small time interval (e.g., 15 minutes). Thereafter, it may be adaptively optimized for each individual patient.

The last of the three features is the SSPD feature. Over a period of several hours, if not several days prior to a seizure, or a first of a series of seizures, there is generally a gradual entrainment among certain critical sites. The present invention exploits this to provide the SSPD feature. Specifically, the SSPD feature is, in accordance with a preferred embodiment of the present invention, implemented in much the same way as the ISW feature, that is, by generating a T-index profile for each of the one or more critical channel groups associated with the selected predictor, and by observing those average T-index profiles. The average T-index profiles are typically generated and observed over a period of several hours or days, rather than minutes.

Figure 10A:
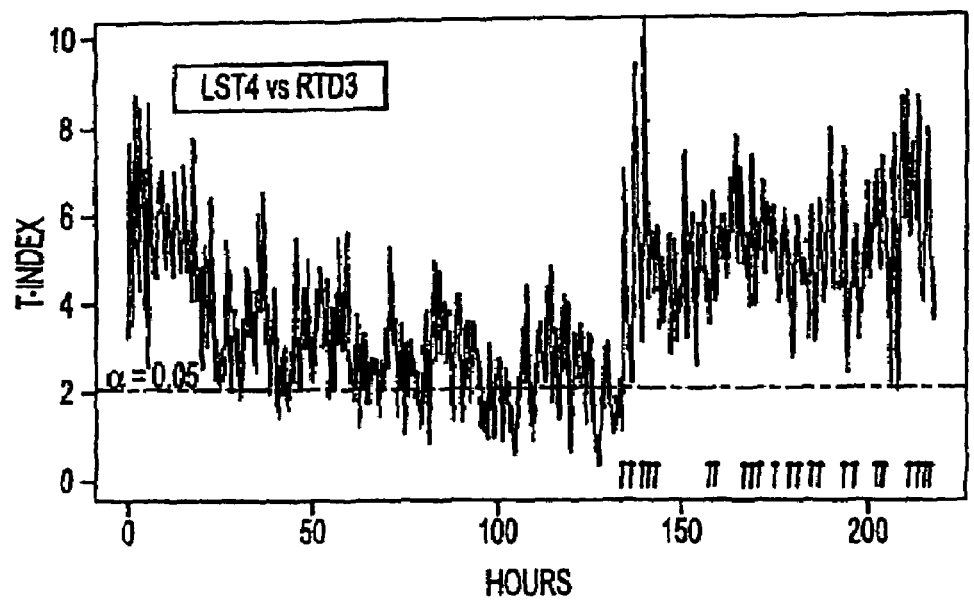
FIGS. 10A and 10B illustrate the T-index profiles associated with two electrode pairs calculated over a 10-day period.
Figure 10B:
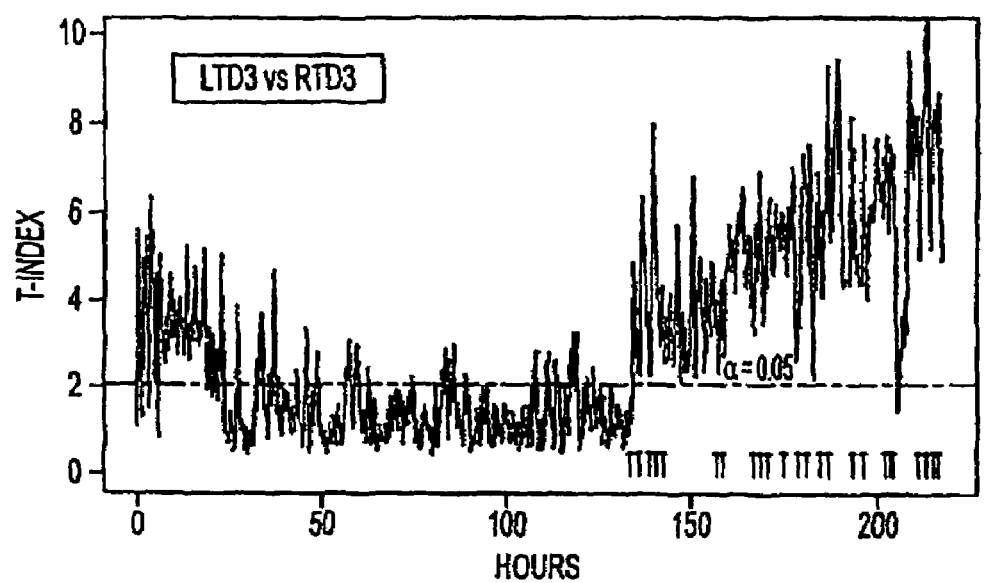

FIGS. 10A and 10B illustrate the average T-index profiles associated with two different electrode pairs calculated over a 10-day period. It will be understood, however, that similar, average T-index profiles might be generated for critical channel groups consisting of two or more channels. The patient was seizure-free during the first 135 hours of the recording. However, over the subsequent 90 hours, the patient experienced 24 seizures, as indicated by the 24 arrows located along the time (hours) axis.

FIG. 10A specifically shows a T-index profile associated with a focal electrode RTD3 and a contralateral subtemporal electrode LST4. For this particular channel pair, dynamic entrainment occurred gradually, where the T-index profile values fell below $T_E$ only after the third day of recording. At the onset of the first seizure, resetting of the affected cortical sites (i.e., disentrainment) begins to occur.

Referring now to FIG. 10B, it is of particular interest that the T-index profile associated with bilateral hippocampal electrodes LTD3 and RTD3 falls below the statistically significant threshold value $T_E$, approximately one (1) day into the recording, thus indicating that the signals associated with the electrode pair are entrained approximately four (4) days prior to the first seizure. Moreover, the signals associated with this pair of electrodes remain mostly entrained until the first seizure, after which, the affected cortical sites begin to reset progressively. Again, the present invention exploits this behavior to provide the SSPD feature. It should be noted that due to the time resolution (i.e., hours) used for FIGS. 10A and 10B, resetting after each individual seizure cannot be visualized in these figures.

As described above, the methods illustrated in FIGS. 3A-3C rely on a comparison between the $STL_{MAX}$ profiles of channel pairs, where each $STL_{MAX}$ profile is derived from a signal measured at a corresponding electrode site. In some instances, it may be beneficial to directly compare the $STL_{MAX}$ profiles corresponding with each group of channels for all or the one selected predictor. In such instances, the groups will typically consist of more than two channels and it may not be appropriate to employ a T-statistic. For example, an F-statistic or F-index statistic (i.e., ANOVA statistic) may be employed instead of a T-statistic, if $STL_{MAX}$ profiles associated with groups of three or more channels are being compared. Yet another alternative is to employ neural network technology and pattern recognition techniques to analyze the level of entrainment between groups of two, three or more $STL_{MAX}$ profiles.

Figure 11:
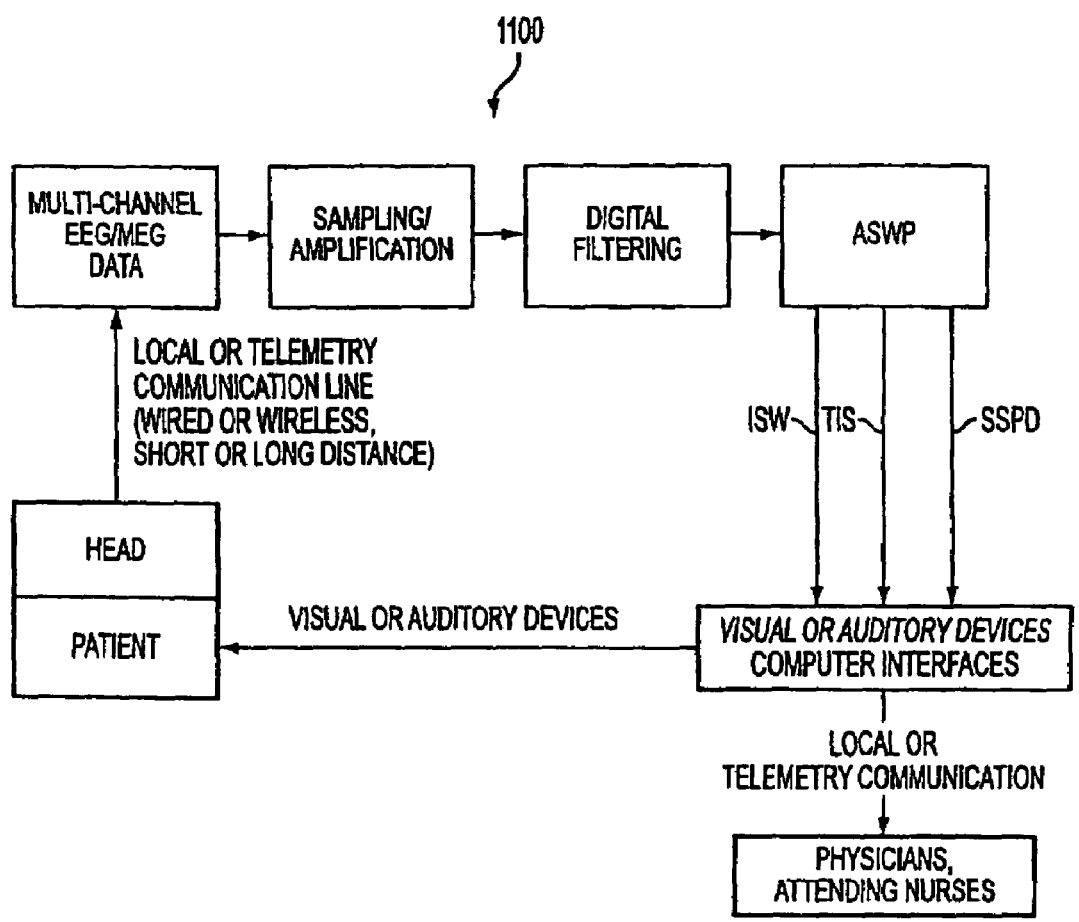
FIG. 11 illustrates an on-line system that incorporates the ISW, SSPD and TISP features of the present invention.

FIG. 11 illustrates an on-line system 1100 that incorporates the various features of the present invention, as described above. The on-line system 1100 may be used in any number of clinical or non-clinical applications, including diagnostic applications, as well as applications relating to patient treatment. For example, the on-line system 1100 may be used to collect and process EEG or MEG signals for subsequent clinical interpretation (e.g., to analyze and determine seizure propagation patterns). The on-line system 1100 may also be used to alert hospital or clinic staff members of an impending seizure, via a local or telemetry link, so that staff members have adequate time to prevent patient injury or provide timely medical intervention to prevent the seizure itself; to observe the seizure; or to prepare for and administer other procedures that must be accomplished during the seizure, such as the administration of radiolabelled ligands or other substances required to obtain ictal SPECT, ictal FMRI, or ictal PET images for pre-surgical diagnostic purposes.

In addition to surgical excision of the epileptogenic focus, current methods for controlling epileptic seizures include pharmacological (i.e., antiepileptic drug) therapy. The currently accepted pharmacological approach is to prescribe fixed doses of one or more antiepileptic drugs (e.g. phenytoin, phenobarbital, carbamazepine, divalproex sodium, etc.) to be taken chronically at fixed time intervals. The objective is to achieve a steady-state concentration in the brain that is high enough to provide optimal seizure control, but low enough to reduce the risk of side-effects.

Figure 12:
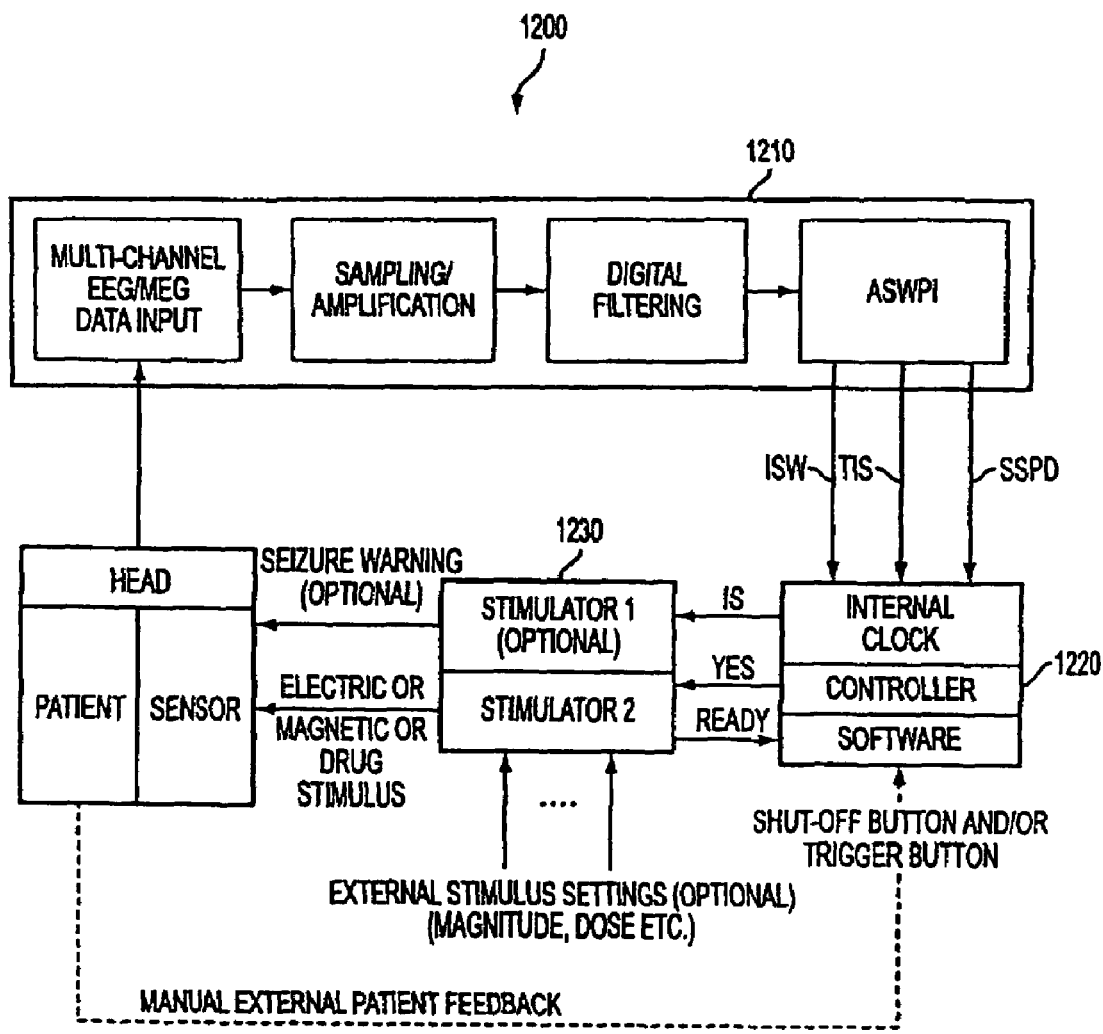
FIG. 12 illustrates a therapeutic intervention system that incorporates an indwelling device capable of providing ISW, SSPD and TISP in accordance with the present invention.

Given the currently accepted pharmacological approach described above, FIG. 12 illustrates an alternative, system level embodiment of the present invention. More particularly, FIG. 12 illustrates a pharmacological antiepileptic seizure system that includes an indwelling device, such as a real-time digital signal processing chip 1210, that contains, among other things, an algorithm that is capable of providing seizure warning and prediction (ASWP), in accordance with the present invention, as described above. As illustrated in FIG. 12, the ISW, TISP, and SSPD signals generated by the indwelling device 1210 are forwarded to a controller 1220. The controller 1220 can then trigger the release of a compound, such as a small dose of an anticonvulsant drug, into the blood stream of the patient from a stimulator 1230 which contains or is connected to an indwelling reservoir. The objective, of course, is to release a small quantity of anticonvulsant drug during the preictal transition stage to abort any impending seizure.

FIG. 12 also illustrates that the therapeutic intervention system 1200 may, in addition to delivering anticonvulsant drug therapy, deliver electric or magnetic stimulation, for example, through a vagal nerve stimulator. Vagal nerve stimulators are currently used to deliver electrical impulses to the vagus nerve in the patient's neck at externally specified intervals, in an arbitrary fashion, with a predetermined duration and intensity. In contrast, the present invention, in accordance with the exemplary embodiment illustrated in FIG. 12, delivers an electrical impulse to the vagus nerve in the neck of specified duration and intensity, but the impulse is delivered only during the preictal transition state. To accomplish this objective, the indwelling device 1210 detects the preictal transition state based on dynamical analysis of ongoing brain electrical activity, as described in detail above. When a preictal state is detected, the indwelling vagal nerve stimulator is triggered and an electrical pulse is delivered to the vagus nerve in the neck. It will be readily apparent, however, to those skilled in the art that devices other than vagal nerve stimulators, for example, deep brain stimulators, may be used in conjunction with the present invention to create brain pacemakers for epileptic patients.

The present invention has been described with reference to a number of exemplary embodiments. However, it will be readily apparent to those skilled in the art that it is possible to embody the invention in specific forms other than those described above without departing from the spirit of the invention. In fact, it will be readily apparent that the present invention may be employed for other medical (e.g., heart pacemakers, stroke diagnosis and prevention, dynamic brain disorders, etc. . . . ), non-medical, non-linear, multidimensional dynamic processes characterized by sudden phase transitions. Accordingly, the various embodiments described above are illustrative, and they should not be considered restrictive in any way. The scope of the invention is given by the appended claims, rather than the preceding description, and all variations and equivalents thereof which fall within the range of the claims are intended to be embraced therein.

What is claimed is:

1. A method of analyzing a multidimensional system comprising the steps of:

acquiring a plurality of signals, each signal representing a corresponding channel that is associated with a different spatial location of the multi-dimensional system;

generating a phase space representation for each channel as a function of the corresponding one of the plurality of signals;

generating a signal profile for each phase space representation, each signal profile reflecting a rate of divergence of the corresponding phase space representation;

choosing a selected predictor from amongst a plurality of possible predictors based on a level of entrainment of critical channel groups associated with each predictor;

for the selected predictor, deriving a signal profile for one or more critical channel groups, each signal profile reflecting a level of correlation between the channels of each critical group; and characterizing the state dynamics of the multidimensional system as a function of the signal profile associated with at least one critical channel group.

2. The method of claim 1 further comprising the step of comparing each signal profile associated with a critical channel group to a threshold value, wherein said step of characterizing the state dynamics of the multidimensional system is based on the result of the comparison.

3. The method of claim 1 further comprising the step of: comparing each signal profile associated with a critical channel group to a disentrainment threshold value and an entrainment threshold value, wherein said step of characterizing the state dynamics of the multidimensional system is based on the result of the comparison.

4. The method of claim 3 further comprising the steps of: determining whether each signal profile associated with a critical channel group exceeded the disentrainment threshold value; and
determining whether each signal profile associated with a critical channel group drops below the entrainment threshold value.

5. The method of claim 4, wherein at least one of said entrainment threshold and said disentrainment threshold is an adaptive parameter.

6. The method of claim 1 further comprising the steps of: detecting a system event indicative of non-chaotic system behavior;
for each of a plurality of predictors, deriving a signal profile for each channel groups, each signal profile reflecting a level of correlation between the channels of each channel group; and
for each of the plurality of predictors, identifying a number of critical channel groups.

7. The method of claim 6 further comprising the step of: choosing the selected predictor from amongst the plurality of predictors as a function of the signal profiles reflecting level of correlation for the critical channel groups associated with each predictor.

8. The method of claim 6 further comprising the step of: after each of a number of system events, updating the number of critical channel groups of each predictor.

9. The method of claim 8 further comprising the step of: choosing the selected predictor from amongst the plurality of predictors as a function of the signal profiles reflecting level of correlation for the critical channel groups associated with each predictor.

10. The method of claim 6, wherein said step of identifying the number of critical channel groups for each predictor is based on the signal values in a limited portion of the level of correlation signal profile associated with each channel group of each predictor, preceding the system event.

11. The method of claim 10, wherein said step of identifying the number of critical channel groups for each predictor is based on the signal values in a limited portion of the level of correlation signal profile associated with each channel group of each predictor, subsequent to the system event.

12. A method of providing seizure warnings comprising the steps of:
acquiring a plurality of time-series signals, each signal associated with a different location of the brain, and where each signal and its corresponding location constitute a corresponding channel;
generating a spatio-temporal response for each channel as a function of a corresponding one of the time-series signals;
generating a signal profile for each spatio-temporal response, each signal profile comprising a sequence of chaoticity values reflecting a rate of divergence of the corresponding spatio-temporal response;
detecting at least one seizure-related event;
after each at least one seizure-related event, determining, for each of a plurality of predictors, a level of entrainment associated with each channel group for each predictor, and based on the level of entrainment associated with each channel group, determining a number of critical channel groups for each predictor;
choosing a selected predictor from amongst the plurality of predictors based on the level of entrainment of the critical channel groups associated with each predictor;
determining when the level of entrainment associated with one or more of the critical channel groups of the selected predictor is statistically significant; and
generating a seizure warning when it is determined that the level of entrainment associated with at least one critical channel group of the selected predictor is statistically significant.

13. The method of claim 12, wherein said step of generating a signal profile for each spatio-temporal response involves generating a sequence of Lyapunov exponent values for each spatio-temporal response.

14. The method of claim 13, wherein the Lyapunov exponent values are short-term Lyapunov exponent values.

15. The method of claim 12, wherein said step of determining, for each of the plurality of predictors, the level of entrainment associated with each channel group is based on the level of entrainment within a time window, the majority of which precedes the at least one seizure-related event, where the at least one seizure-related event is an entrainment transition event.

16. The method of claim 12, wherein said step of determining, for each of the plurality of predictors, the level of entrainment associated with each channel group is based on the level of entrainment within a first time window preceding the at least one seizure-related event and a second time window subsequent to the at least one seizure-related event, where the at least one seizure-related event is a seizure.

17. The method of claim 12, wherein said step of determining, for each of the plurality of predictors, the level of entrainment associated with each channel group comprises the step of:
generating a sequence of T-index values for each channel group.

18. The method of claim 12, wherein said step of choosing the selected predictor from amongst the plurality of predictors comprises the step of:
comparing the level of entrainment associated with the critical channel groups of each of the plurality of the predictors.

19. The method of claim 18, wherein the selected predictor has critical channel groups that exhibit relatively high levels of entrainment prior to seizures as compared to the critical channel groups associated with other predictors.

20. The method of claim 19, wherein the selected predictor has critical channel groups that exhibit disentrainment following seizures as compared to the critical channel groups associated with other predictors.

21. The method of claim 12, wherein the selected predictor has critical channel groups that exhibit relatively high levels of entrainment during entrainment transition events as compared to the critical channel groups associated with other predictors.

22. The method of claim 12, wherein the selected predictor has critical channel groups that exhibit relatively high levels of entrainment prior seizures and entrainment transition events, and exhibit disentrainment following seizures and entrainment transition events.

23. The method of claim 12, wherein said step of determining when the level of entrainment associated with one or more of the critical channel groups of the selected predictor is statistically significant comprises the step of:
  comparing the level of entrainment associated with each critical channel group of the selected predictor to at least one threshold value.

24. The method of claim 23, wherein said step of comparing the level of entrainment associated with each critical channel group of the selected predictor to at least one threshold value comprises the step of:
  comparing the level of entrainment associated with each critical channel group of the selected predictor to an entrainment threshold value.

25. The method of claim 24, wherein said step of comparing the level of entrainment associated with each critical channel group of the selected predictor to at least one threshold value further comprises the step of:
  comparing the level of entrainment associated with each critical channel group of the selected predictor to a disentrainment threshold value, and wherein a determination that the level of entrainment associated with one or more of the critical channel groups of the selected predictor is statistically significant involves a determination that the level of entrainment has exceeded the disentrainment threshold value and subsequent thereto dropped below the entrainment threshold.

26. The method of claim 12 further comprising the step of:
  generating a seizure prediction when it is determined that the level of entrainment associated with at least one critical channel group of the selected predictor is statistically significant.

27. The method of claim 12 further comprising the step of:
  updating each critical channel group of the selected predictor after each subsequent seizure-related event.

28. The method of claim 27, wherein said step of updating each critical channel group of the selected predictor comprises the step of:
  reselecting one or more critical channel groups for the selected predictor as a function of the level of entrainment, associated with each channel group of the selected predictor, within a time window, the majority of which precede the seizure-related event, where the seizure-related event is an entrainment transition event.

29. The method of claim 27, wherein said step of updating each critical channel group of the selected predictor comprises the step of:
  reselecting one or more critical channel groups for the selected predictor as a function of the level of entrainment, associated with each channel group of the selected predictor, within a first tune window preceding the seizure-related event and a second time window following the seizure-related event, where the seizure-related event is a seizure.

30. A method of providing seizure warnings comprising the steps of:
  choosing a selected predictor from amongst a plurality of predictors;
  acquiring a plurality of time-series signals, each signal associated with a different location of the brain, and where each signal and its corresponding location constitute a corresponding channel;
  generating a spatio-temporal response for each channel as a function of a corresponding one of the time-series signals;
  generating a signal profile for each spatio-temporal response, each signal profile comprising a sequence of chaoticity values reflecting a rate of divergence of the corresponding spatio-temporal response;
  determining whether the level of entrainment associated with one or more critical channel groups of the selected predictor is statistically significant; and
  generating a seizure warning if it is determined that the level of entrainment associated with one or more critical channel groups of the selected predictor is statistically significant.

31. The method of claim 30, wherein said step of determining whether the level of entrainment associated with one or more critical channel groups of the selected predictor is statistically significant comprises the step of:
  comparing the level of entrainment associated with each of the one or more critical channel groups of the selected predictor to at least one threshold value.

32. The method of claim 31, wherein said step of comparing the level of entrainment associated with each of the one or more critical channel groups of the selected predictor to at least one threshold value comprises the step of:
  comparing the level of entrainment associated with each of the one or more critical channel groups of the selected predictor to an entrainment threshold value.

33. The method of claim 32, wherein said step of comparing the level of entrainment associated with each of the one or more critical channel groups of the selected predictor to at least one threshold value further comprises the step of:
  comparing the level of entrainment associated with each of the one or more critical channel groups of the selected predictor to a disentrainment threshold value, and wherein a determination that the level of entrainment associated with one or more of the critical channel groups of the selected predictor is statistically significant involves a determination that the level of entrainment has exceeded the disentrainment threshold value and subsequent thereto dropped below the entrainment threshold.

34. The method of claim 30 further comprising the step of:
  generating a seizure prediction when it is determined that the level of entrainment associated with one or more critical channel groups of the selected predictor is statistically significant.

35. The method of claim 30 further comprising the step of:
  updating the one or more critical channel groups of the selected predictor after each seizure-related event.

36. The method of claim 35, wherein said step of updating the one or more critical channel groups of the selected predictor comprises the step of:
  reselecting the one or more critical channel groups of the selected predictor as a function of the level of entrainment, associated with each channel group of the selected predictor, within a time window, the majority of which precedes the seizure-related event, where the seizure-related event is an entrainment transition event.

37. The method of claim 35, wherein said step of updating the one or more critical channel groups of the selected predictor comprises the step of:
  reselecting the one or more critical channel groups of the selected predictor as a function of the level of entrainment, associated with each channel group of the selected predictor, within a first time window preceding the seizure-related event and a second time window following the seizure-related event, where the seizure-related event is a seizure.

38. An apparatus providing seizure interdiction comprising:

a plurality of sensors, each configured for acquiring a time-series signal associated with a corresponding location of a patient's brain;

processing means for generating a seizure warning based on the time-series signals, said processing means comprising, means for receiving the time-series signals; wherein each time-series signal along with the corresponding location of the patient's brain constitutes a separate channel;

means for generating a phase space representation for each channel as a function of the conesponding one of the plurality of signals;

means for generating a signal profile for each phase space representation, each signal profile reflecting a rate of divergence of the corresponding phase space representation;

means for choosing a selected predictor from amongst a plurality of possible predictors;

means for deriving a signal profile for each of a number of critical channel groups associated with the selected predictor, each signal profile reflecting a level of entrainment among the channels of each critical channel group;

means for determining whether a level of entrainment associated with one or more critical channel groups of the selected predictor is statistically significant;

means for generating a seizure warning if it is determined that the level of entrainment associated with one or more critical channel groups of the selected predictor is statistically significant; and a seizure interdiction device coupled to said processing means, said seizure interdiction device comprising means for delivering antiseizure treatment to the patient if a seizure warning signal is generated.

39. The apparatus of claim 38, wherein said processing means further comprises:

means for updating the one or more critical channel groups for the selected predictor after each of a number of seizure-related events.

40. The apparatus of claim 39, wherein said means for updating the one or more critical channel groups comprises:

means for reselecting the one or more critical channel groups of the selected predictor as a function of the level of entrainment, associated with each channel group of the selected predictor, within a tune window, the majority of which precedes the seizure-related event, where the seizure-related event is an entrainment transition event.

41. The method of claim 39, wherein said means for updating the one or more critical channel groups comprises:

means for reselecting the one or more critical channel groups of the selected predictor as a function of the level of entrainment, associated with each channel group of the selected predictor, within a first time window preceding the seizure-related event and a second time window following the seizure-related event, where the seizure-related event is a seizure.

* * * * *

UNITED STATES PATENT AND TRADEMARK OFFICE
CERTIFICATE OF CORRECTION

PATENT NO. : 7,373,199 B2  Page 1 of 1
APPLICATION NO. : 10/648354
DATED : May 13, 2008
INVENTOR(S) : Sackellares et al.

It is certified that error appears in the above-identified patent and that said Letters Patent is hereby corrected as shown below:

Column 1, line 19, after "DEVELOPMENT" add
--This invention was made with United States Government support. The United States Government has certain rights in the invention.--

Signed and Sealed this

Fifth Day of August, 2008

JON W. DUDAS
*Director of the United States Patent and Trademark Office*

UNITED STATES PATENT AND TRADEMARK OFFICE
Certificate

Patent No. 7,373,199 B2            Patented: May 13, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: James Chris Sackellares, Gainesville, FL (US); Leonidas D. Iasemidis, Scottsdale, AZ (US); Deng-Shan Shiau, Gainesville, FL (US); Linda Dance, Gainesville, FL (US); Pat M. Pardalos, Gainesville, FL (US); and Wanpracha A. Chaovalit-wongse, Hillsborough, NJ (US).

Signed and Sealed this Twenty-fourth Day of November 2009.

<div align="right">

CHARLES A. MARMOR, II
*Supervisory Patent Examiner*
Art Unit 3735

</div>